(12) United States Patent
Rosenberg et al.

(10) Patent No.: US 8,295,918 B2
(45) Date of Patent: Oct. 23, 2012

(54) SYSTEMS AND METHODS FOR ACTIVATING AND CONTROLLING IMPEDANCE-BASED DETECTION SYSTEMS OF IMPLANTABLE MEDICAL DEVICES

(75) Inventors: Stuart Rosenberg, Castaic, CA (US); Cecilia Q. Xi, San Jose, CA (US); Yelena Nabutovsky, Sunnyvale, CA (US); Brian J. Wenzel, San Jose, CA (US); Jong Gill, Valencia, CA (US); William Hsu, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 135 days.

(21) Appl. No.: 13/035,773

(22) Filed: Feb. 25, 2011

(65) Prior Publication Data

US 2012/0221066 A1    Aug. 30, 2012

(51) Int. Cl.
*A61B 5/04*        (2006.01)
(52) U.S. Cl. ........................................................ 600/509
(58) Field of Classification Search .................... 600/509
See application file for complete search history.

(56) References Cited

U.S. PATENT DOCUMENTS

| | | | |
|---|---|---|---|
| 5,643,327 A | 7/1997 | Dawson et al. | 607/24 |
| 6,249,705 B1 | 6/2001 | Snell | 607/59 |
| 6,473,647 B1 | 10/2002 | Bradley | 607/27 |
| 6,480,733 B1 | 11/2002 | Turcott | 600/516 |
| 6,512,952 B2 | 1/2003 | Stahmann et al. | 607/9 |
| 6,628,988 B2 | 9/2003 | Kramer et al. | 607/9 |
| 6,643,546 B2 | 11/2003 | Mathis et al. | 607/9 |
| 6,658,292 B2 | 12/2003 | Kroll et al. | 607/19 |
| 7,072,715 B1 | 7/2006 | Bradley | 607/17 |
| 7,149,579 B1 | 12/2006 | Koh | 607/19 |
| 7,272,436 B2 | 9/2007 | Gill et al. | 600/513 |
| 7,272,443 B2 | 9/2007 | Min et al. | 607/17 |
| 7,336,999 B1 | 2/2008 | Koh | 607/27 |
| 7,430,447 B2 | 9/2008 | Min et al. | 607/17 |
| 7,440,804 B1 | 10/2008 | Min et al. | 607/28 |
| 7,628,757 B1 | 12/2009 | Koh | 600/484 |
| 7,676,264 B1 | 3/2010 | Pillai et al. | 607/9 |
| 7,794,404 B1 * | 9/2010 | Gutfinger et al. | 600/486 |
| 2005/0216067 A1 | 9/2005 | Min et al. | 607/17 |
| 2008/0024293 A1 | 1/2008 | Stylos | 340/532 |
| 2009/0062729 A1 | 3/2009 | Woo | 604/66 |
| 2009/0062730 A1 | 3/2009 | Woo | 604/66 |
| 2009/0254140 A1 | 10/2009 | Rosenberg et al. | 607/17 |
| 2009/0287267 A1 | 11/2009 | Wenzel et al. | 607/9 |
| 2010/0030292 A1 | 2/2010 | Sarkar et al. | 607/6 |
| 2010/0069778 A1 | 3/2010 | Bornzin et al. | 600/547 |
| 2010/0152801 A1 | 6/2010 | Koh et al. | 607/9 |
| 2010/0280397 A1 | 11/2010 | Feldman et al. | 600/486 |

FOREIGN PATENT DOCUMENTS

WO    WO 2010/014070    2/2010

* cited by examiner

*Primary Examiner* — George Manuel

(57) ABSTRACT

Techniques are provided for use with implantable medical devices for addressing encapsulation effects, particularly in the detection of cardiac decompensation events such as heart failure (HF) or cardiogenic pulmonary edema (PE.) In one example, during an acute interval following device implant, cardiac decompensation is detected using heart rate variability (HRV), ventricular evoked response (ER) or various other non-impedance-based parameters that are insensitive to component encapsulation effects. During the subsequent chronic interval, decompensation is detected using intracardiac or transthoracic impedance signals. In another example, the degree of maturation of encapsulation of implanted components is assessed using impedance frequency-response measurements or based on the frequency bandwidth of heart sounds or other physiological signals. In this manner, impedance-based HF/PE detection systems can be activated as soon as component encapsulation has matured, without necessarily waiting until completion of a preset post-implant maturation interval, often set to forty-five days or more.

20 Claims, 17 Drawing Sheets

SYSTEMS AND METHODS FOR ACTIVATING AND CONTROLLING IMPEDANCE-BASED DETECTION SYSTEMS OF IMPLANTABLE MEDICAL DEVICES

FIELD OF THE INVENTION

The invention generally relates to implantable medical devices, such as pacemakers, implantable cardioverter/defibrillators (ICDs) or cardiac resynchronization therapy devices (CRTs) and, in particular, to techniques for detecting and tracking heart failure (HF), cardiogenic pulmonary edema (PE) or related cardiac decompensation events within patients in which such devices are implanted.

BACKGROUND OF THE INVENTION

Cardiac decompensation generally refers to the failure of the heart to maintain adequate blood circulation due, for example, to HF or other medical ailments. A particularly severe form of heart failure is congestive heart failure (CHF) wherein the weak pumping of the heart leads to build-up of fluids in the lungs and other organs and tissues. The build-up of fluids in the lungs due to poor heart function is referred to as cardiogenic PE. Herein, HF, CHF and cardiogenic PE are all considered to be cardiac decompensation events.

It is highly desirable to detect cardiac decompensation events within a patient and to track the progression thereof using implantable medical devices so that appropriate therapy can be provided. At least some techniques have been developed for detecting HF/PE events and delivering responsive therapy that exploit electrical impedance signals (or related signals such as admittance or immittance) measured within the patient.

See, e.g., U.S. Patent Application 2010/0069778 of Bornzin et al., entitled "System and Method for Monitoring Thoracic Fluid Levels based on Impedance using an Implantable Medical Device"; U.S. Pat. No. 7,628,757 to Koh, entitled "System and Method for Impedance-Based Detection of Pulmonary Edema and Reduced Respiration using an Implantable Medical System"; and U.S. Pat. No. 7,272,443 to Min et al., entitled "System and Method for Predicting a Heart Condition based on Impedance Values using an Implantable Medical Device." See, also, U.S. patent application Ser. No. 11/558,194, of Panescu et al., filed Nov. 9, 2006, entitled "Closed-Loop Adaptive Adjustment of Pacing Therapy based on Cardiogenic Impedance Signals Detected by an Implantable Medical Device." Still further, see U.S. Patent Application 2009/0287267 of Wenzel et al., entitled "System and Method for Estimating Electrical Conduction Delays from Immittance Values Measured using an Implantable Medical Device," which described techniques for using impedance to evaluate conduction delays that can be converted to LAP values for tracking HF.

Although impedance-based HF/PE techniques are generally effective during a chronic implant phase beginning a few months after device implant, problems can arise during an acute phase during the first month or two following device implant. During the acute phase, the electrodes used by the device to detect impedance are subject to on-going tissue encapsulation. During that interval, changes in tissues surrounding the electrodes—including tissues surrounding the housing of the device itself—can greatly affect the impedance values measured using the electrodes, typically rendering impedance-based HF/PE detection systems unreliable and unusable.

In this regard, the human body typically encapsulates the leads and device during the first thirty to sixty days following the implantation. The encapsulation tissue changes the local impedance characteristics surrounding the lead electrodes, as well as the device housing electrode. It is now believed that the majority of the impedance characteristics occur within about one centimeter of the electrodes used to measure the impedance. Given that the majority of the signal occurs near the electrode and the encapsulation occurs on or near the surface of the electrode, it is expected that measured impedance signals will vary with changes in encapsulation. This applies to both transthoracic or intrathoracic impedance signals (measured between the device housing and electrodes on or within the heart) and intracardiac impedance signals (measured between a pair of electrodes on or within the heart.) Herein, transthoracic impedance signals are also referred to as "PE impedance signals," since the transthoracic signals are used to detect PE. Intracardiac impedance signals are also referred to herein as cardiogenic impedance (CI) signals, since the intracardiac signals exhibit variations representative of the beating of the chambers of the heart.

Moreover, the magnitude and duration of changes to impedance during encapsulation can depend greatly on the individual patient's genetics, immune system, the health of the patient, the affects of the steroids, patient medications, and many other factors. Given all of these parameters, it is currently not feasible to determine a priori when impedance signals will stabilize. Therefore, at least some state-of-the-art HF/PE impedance detection systems are programmed to ignore the first forty-five days or so of impedance data, post-implant. That is, a moratorium is imposed within algorithms of the device against collecting impedance data during that initial interval for the purposes of detecting HF/PE. (Impedance may be measured for other reasons, such as to detect lead failure.) Furthermore, many HF/PE impedance detection systems employ a fourteen day moving average as a baseline for use in detecting HF/PE. Therefore, once the encapsulation process is complete, such systems need an additional fourteen days to fully stabilize before HF/PE detection can begin, which means that such systems do not detect or respond to cardiac decompensation events during the first sixty days after implant, leaving the patient potentially vulnerable. It is noted that not all devices ignore the first forty-five days of impedance data. Some devices may ignore only the first thirty days of data. Nor do all devices employ a fourteen day "moving average" window. Typically, though, HF/PE impedance-based detection systems are not activated until about forty-five to sixty days post implant.

It would be desirable to provide techniques for detecting HF, PE or other cardiac decompensation events that can be employed during the post-implant acute phase. It would also be desirable to determine within a particular patient whether impedance-based HF/PE detection systems can be safely activated before completion of the typical forty-five to sixty-day post-implant interval. It is to these ends that aspects of the present invention are directed.

SUMMARY OF THE INVENTION

In accordance with a first aspect of the invention, an exemplary method is provided for use with an implantable medical device for addressing encapsulation effects, particularly in the detection of cardiac decompensation events such as HF and cardiogenic pulmonary edema PE. Briefly, during an acute interval or phase following device implant, cardiac decompensation events are detected within the patient using detection parameters that are relatively insensitive to component encapsulation effects, particularly various non-impedance based detection parameters. Then, following the acute interval, cardiac decompensation events are detected using parameters that are relatively more sensitive to component encapsulation effects, such as intracardiac impedance (sometimes also referred to as "cardiogenic impedance" (CI)) parameters or transthoracic (PE) impedance parameters. That is, following the acute interval, an otherwise conventional impedance-based HF/PE detection system may be activated to take over HF/PE detection.

In an illustrative embodiment, the implantable device is a pacemaker, ICD or CRT device. The cardiac decompensation events that are detected by the device include HF, CHF or cardiogenic PE. During the acute interval following device implant, cardiac decompensation is detected based on changes in heart rate variability (HRV), ventricular evoked response (ER), atrioventricular (AV/PV) delay and interventricular (VV) delay or other non-impedance based detection factors or parameters. The detection of a possible cardiac decompensation event during the acute interval can be supplemented or corroborated using patient posture signals, patient activity signals or blood pressure signals. During the subsequent chronic interval, cardiac decompensation is detected using the aforementioned CI or PE impedance parameters or based on some combination of impedance and non-impedance based parameters.

In one particular example, the acute interval is deemed to have ended sixty days after implant—a time period set based on a forty-five day maturation "moratorium" period combined with a subsequent fourteen-day moving average window for collecting impedance measurements. In other examples, a shorter time period is set based on a thirty day moratorium plus the fourteen-day moving average window. In still other examples, the end of the acute interval is detected based on impedance signal stability or other factors. In either case, the transition from non-impedance-based parameters (such as HRV and ER) to impedance-based parameters (such as CI or PE signals) can be made gradually by incrementing the weight of impedance-based parameters relative to the weight of non-impedance-based parameters or can be performed immediately by simply switching from one to the other. Preferably, to detect a cardiac decompensation event such as HF or cardiogenic PE, the device uses one or more thresholds against which the various measured parameters are compared. These thresholds can vary based on the medical conditions to be detected, the particular detection parameters used and on the amount of time since implant. Moving average impedance windows can be exploited that gradually increase in duration up to a preferred length upon the completion of the acute interval.

Thus, in accordance with the first aspect of the invention, various techniques are provided that allow for cardiac decompensation events to be detected during the acute phase using, e.g., non-impedance-based parameters such as HRV and ER.

In accordance with a second aspect of the invention, an exemplary method is provided for use with an implantable medical device for determining whether the degree of maturation of encapsulation has reached an acceptable level to permit the use of impedance-based detection techniques. Briefly, impedance-based parameters such as CI or PE signals are detected following device implant. The degree of maturation of encapsulation of components of the implanted device is assessed using the impedance-based parameters. The device then determines whether the degree of maturation has reached an acceptable level and, if so, impedance-based device functions are controlled or activated in response thereto. The impedance-based functions that are activated can be, for example, impedance-based HF/PE detection systems or procedures. In this manner, the impedance-based HF/PE detection systems of the implantable device can be activated as soon as encapsulation has matured, without necessarily waiting until completion of the typical forty-five to sixty-day post-implant moratorium.

In an illustrative embodiment of the second aspect of the invention, the implantable device has one or more electrode pairs subject to encapsulation effects. The degree of maturation of encapsulation of a particular electrode pair is performed by determining an impedance response for the electrodes as a function of frequency and then determining the degree of maturation of tissues surrounding the electrodes based on the impedance frequency response. For example, changes in the magnitude or phase of impedance as a function of frequency can be assessed. The changes are then compared against lookup tables to identify the type of tissue surrounding the electrodes, which might be blood, thrombus, inflammatory tissue, myocardium, fibrosis or endothelium. The degree of maturation is then assessed based on the type of encapsulating tissue. For example, if the tissue surrounding an electrode is found to be subacute inflammatory tissue, then encapsulation has not yet matured. Conversely, if the tissue surrounding the electrode is found to be chronic fibrotic tissue, then encapsulation is deemed to have matured and the electrode can be reliably used to detect impedance signals for the purposes of detecting HF, cardiogenic PE or other cardiac decompensation events. In other examples, the maturation of encapsulation is instead assessed based on the degree of stability of the impedance signals, with greater stability being associated with a greater degree of encapsulation maturity. Still further, in some examples, the thickness of overgrowth tissues encapsulating the electrodes can be assessed.

Depending upon the particular embodiment, the impedance-based parameters used to assess the maturity of encapsulation are measured by applying impedance detection pulses between selected electrode pairs or by applying low-level high-frequency alternating current (AC) signals. In either case, a voltage signal representative of impedance is then measured using a selected electrode pair or another pair of electrodes coupled to the device. The voltage signal is then used to obtain phase and amplitude impedance information.

To assess the maturity of encapsulation of the implantable device itself, the housing of the device can be equipped with two or more "device can" electrodes, which are employed as an electrode pair for assessing encapsulation effects in the device pocket. Further, the similarity or difference in impedance signal between the can and each of two or more distant and/or large electrodes (for example, can-to-RV coil and can-to-SVC coil) may be employed to ascertain the maturity of encapsulation in the device pocket. Still further, the device can be equipped with various internal physiological sensors—such as acoustic sensors or 3D accelerometers—that can be used to assess the degree of maturation of encapsulation of the device housing based on frequency bandwidths of detected signals. For example, the frequency bandwidth of heart sounds or respiration sounds detected by an acoustic sensor can be used to assess the type of tissue in the device pocket.

System, apparatus and method examples of these and other techniques are described below.

BRIEF DESCRIPTION OF THE DRAWINGS

The above and further features, advantages and benefits of the invention will be apparent upon consideration of the descriptions herein taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of Implantable Medical System

Figure 1:
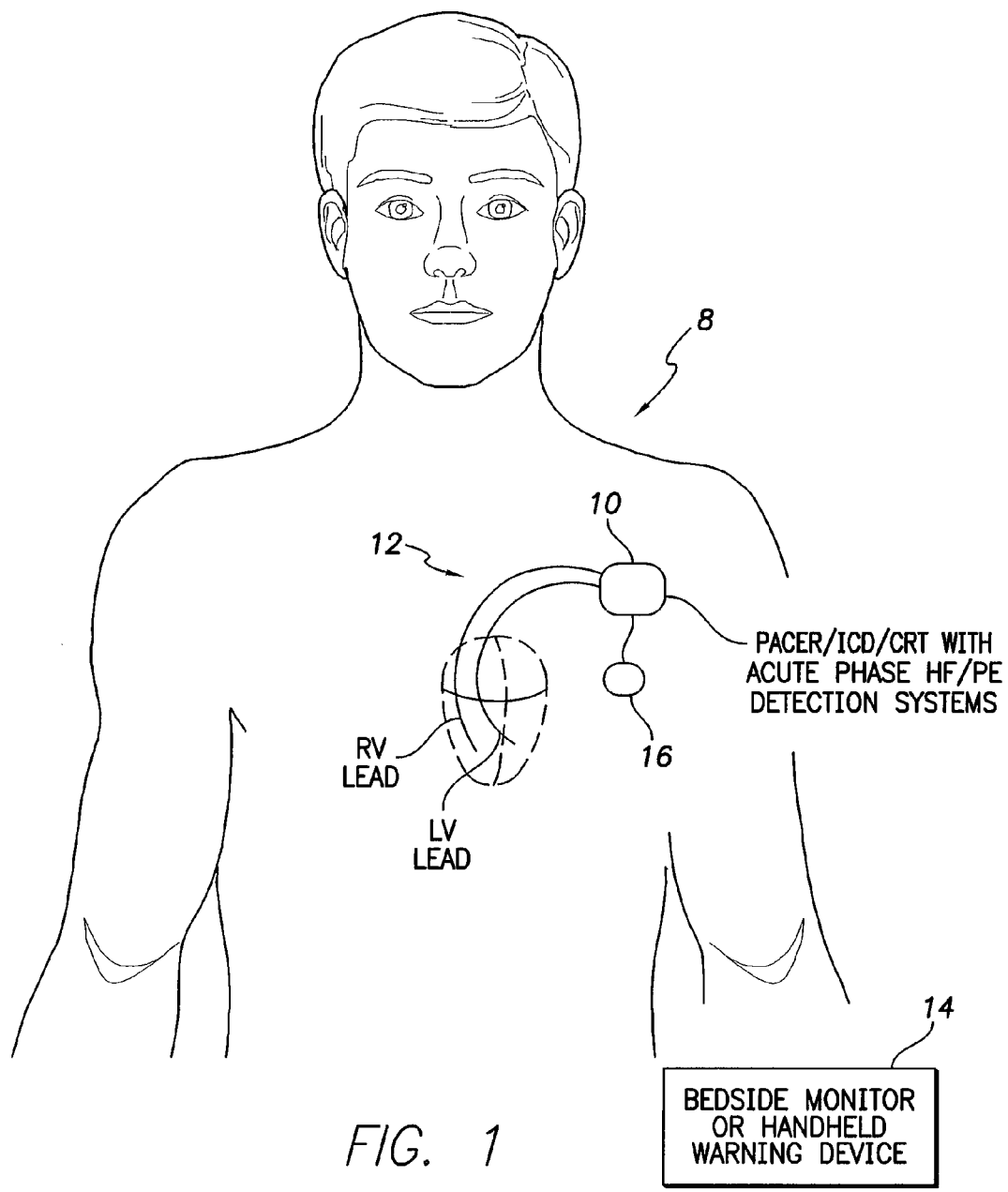
FIG. 1 illustrates pertinent components of an implantable medical system having a pacer/ICD/CRT device equipped with encapsulation-responsive acute phase HF/PE detection systems.

FIG. 1 illustrates an implantable medical system 8 having a pacemaker, ICD, or CRT device 10 (herein "pacer/ICD") equipped with acute phase HF/PE detection systems operative to detect cardiac decompensation events such as HF and cardiogenic PE during an initial acute phase following device implant using impedance or other electrical signals measured via a set of cardiac pacing/sensing leads 12 or using various physiological sensors. A stylized representation of two cardiac pacing/sensing leads is provided In FIG. 1. A more complete illustration of a set of leads is provided in FIG. 15, discussed below. In one example of the operation of the device, various non-impedance-based parameters, such as HRV and ER, are employed during the acute phase to detect the onset or progression of HF, PE or other medical conditions. In another example, impedance and/or physiological signals are used to assess the maturity of encapsulation of the electrodes to determine whether impedance-based HF/PE detection systems or algorithms can be activated during what would otherwise be regarded as the acute phase. One such algorithm is a pulmonary congestion monitoring algorithm called CorVue™. CorVue™ allows for the continuous monitoring of pulmonary fluid retention.

Upon detection of a cardiac decompensation event, warning signals may be generated, diagnostic information stored and/or therapy delivered. Warning signals may be generated using either a warning device internal to pacer/ICD 10 or using an external bedside monitor 14. The internal warning device may be a vibrating device or a "tickle" voltage device that, in either case, provides perceptible stimulation to the patient to alert the patient so that the patient may consult a physician. In one example, once the tickle warning is felt, the patient positions an external handheld device above his or her chest, such as a personal advisory module (PAM), not separately shown. The handheld device receives short-range telemetry signals from the implanted device and provides audible or visual verification of the warning signal. The handheld warning device thereby provides confirmation of the warning to the patient, who might be otherwise uncertain as to the reason for the internally generated warning signal. For further information regarding this type of warning/notification technique, see U.S. Pat. No. 7,272,436 to Gil et al.

If a bedside monitor is provided, the bedside monitor provides audible or visual alarm signals to alert the patient as well as textual or graphic displays. In addition, diagnostic information pertaining to heart failure is transferred to the bedside monitor or is stored within the pacer/ICD for subsequent transmission to an external programmer (see FIG. 17) for review by a physician or other medical professional. External programmers are typically used during follow-up sessions with the patient wherein a clinician downloads information from the implanted device, reviews the information and then adjusts the control parameters of the implanted device, if needed, via the programmer. Bedside monitors typically download information more frequently, such as once per evening, and can be equipped to relay the most pertinent information to the patient's physician via a communication network. In any case, the physician may then prescribe any other appropriate therapies to address the condition. The physician may also adjust the operation of the pacer/ICD to activate, deactivate or otherwise control any therapies that are automatically applied. The bedside monitor may be directly networked with a centralized computing system, such as the HouseCall™ system or the Merlin.Net system of St. Jude Medical, for immediately notifying the physician of any significant increase in LAP. Networking techniques for use with implantable medical systems are set forth, for example, in U.S. Pat. No. 6,249,705 to Snell, entitled "Distributed Network System for Use with Implantable Medical Devices."

Upon detection of a cardiac decompensation event, various forms of therapy may be activated, adjusted or otherwise controlled by the pacer/ICD. If the implanted system is equipped with a drug pump 16, appropriate medications may be automatically administered to address the decompensation. Alternatively, if a drug pump is not available, the patient may be provided with instructions via the bedside monitor as to what dosage to take for various heart failure medications. Exemplary heart failure medications include angiotensin-converting enzyme (ACE) inhibitors such as captopril, enalapril, lisinopril and quinapril, diuretics, digitalis, nitrates, and other compounds. Depending upon the particular medication, alternative compounds (e.g., intravenous or subcutaneous agents) may be required for use in connection with an implantable drug pump. Routine experimentation may be employed to identify medications for treatment of heart failure or other conditions that are safe and effective for use in connection with an implantable drug pump. Dosages may be titrated based upon the severity of decompensation. Various techniques may be employed to confirm the detection of heart failure (or other medical conditions) made by the pacer/ICD before warnings are generated or any therapy is delivered.

If so equipped, CRT therapy or other forms of electrical cardiac rhythm management therapy may be initiated and controlled by the pacer/ICD. CRT and related therapies are discussed in, for example, U.S. Pat. No. 6,643,546 to Mathis et al., entitled "Multi-Electrode Apparatus and Method for Treatment of Congestive Heart Failure"; U.S. Pat. No. 6,628,988 to Kramer et al., entitled "Apparatus and Method for Reversal of Myocardial Remodeling with Electrical Stimulation"; and U.S. Pat. No. 6,512,952 to Stahmann et al., entitled "Method and Apparatus for Maintaining Synchronized Pacing". CRT parameters may be adaptively adjusted by the device to improve the effectiveness of CRT using techniques set forth in the Panescu et al. patent application, "Closed-Loop Adaptive Adjustment of Pacing Therapy based on Cardiogenic Impedance Signals Detected by an Implantable Medical Device," cited above. See, also, U.S. Patent Application 2009/0254140 of Rosenberg et al., entitled "Cardiac Resynchronization Therapy Optimization using Parameter Estimation from Realtime Electrode Motion Tracking," and related patent applications. Still further, see, U.S. Patent Application 2010/0152801 of Koh et al., "Cardiac Resynchronization Therapy Optimization Using Vector Measurements Obtained from Realtime Electrode Position Tracking," and related patent applications.

Additionally, the pacer/ICD performs various standard operations, such as delivering demand based atrial or ventricular pacing, overdrive pacing therapy, or antitachycardia pacing (ATP). The pacer/ICD also monitors for ventricular fibrillation and delivers defibrillation shocks in response thereto.

Hence, FIG. 1 provides an overview of an implantable medical system capable of: detecting HF or other conditions during the acute phase following device implant (as well as during the subsequent chronic phase); delivering any appropriate warning/notification signals; and selectively delivering medications, when warranted. Embodiments may be implemented that do not necessarily perform all of these functions. For example, embodiments may be implemented that detect cardiac decompensation but do not automatically initiate or adjust therapy. Moreover, systems provided in accordance with the invention need not include all of the components shown in FIG. 1. In many cases, the system will include only a pacemaker, ICD, CRT and its respective leads. Warning devices and drug pumps are not necessarily implanted. These are just a few exemplary embodiments. No attempt is made herein to describe all possible combinations of components that may be provided in accordance with the general principles of the invention.

In addition, note that the particular locations of the implanted components shown in FIG. 1 are stylized and may not necessarily correspond to actual implant locations. Although internal signal transmission lines provided are illustrated in FIG. 1 for interconnecting the various implanted components, wireless signal transmission may alternatively be employed.

HF/PE Detection During Acute Phase Using Non-Impedance Signals

Figure 2:
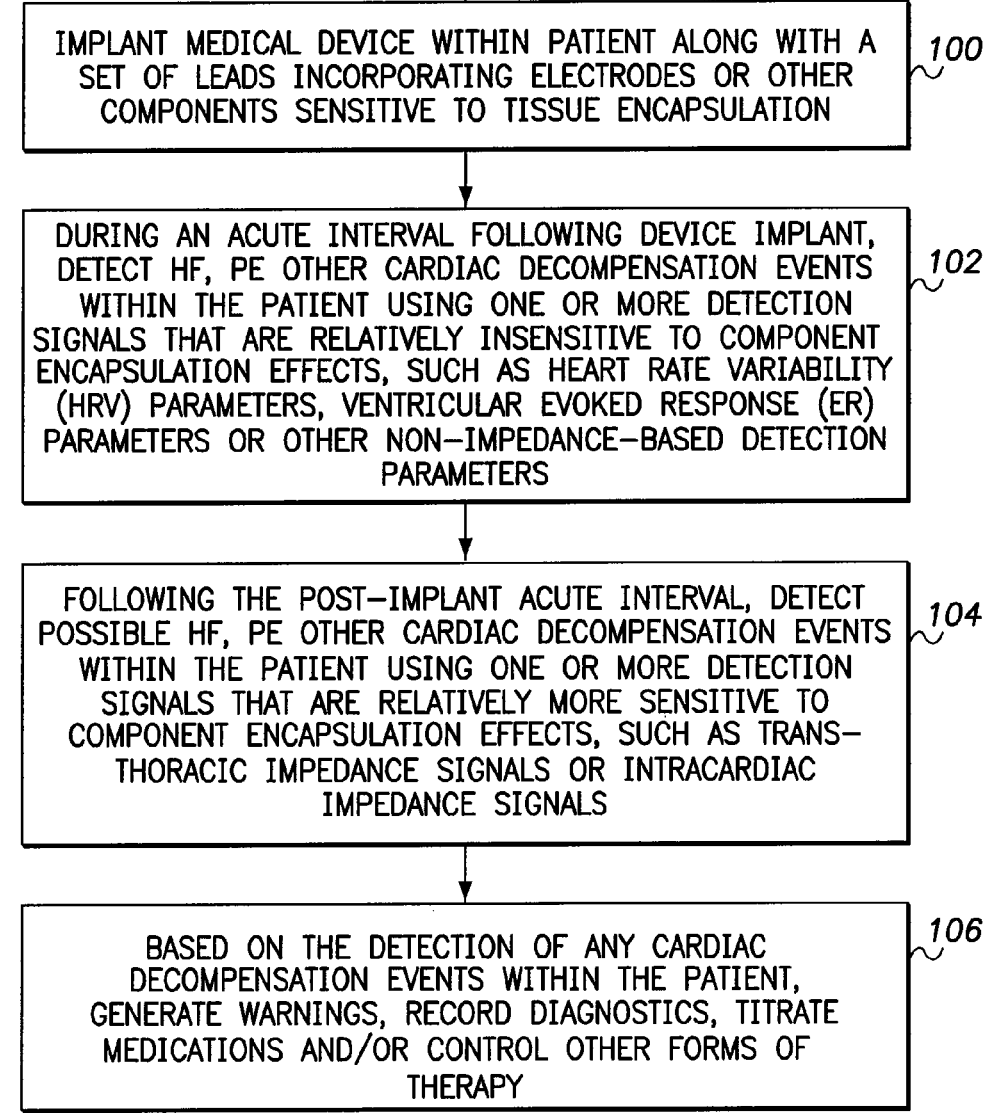
FIG. 2 provides an overview of a method performed by the system of FIG. 1 for detecting HF/PE using non-impedance-based parameters during the acute phase.

FIG. 2 provides a broad overview of techniques that may be performed for detecting cardiac decompensation during the acute phase. Beginning at step 100, a pacer/ICD is implanted within a patient along with a set of leads incorporating electrodes or other components sensitive to tissue encapsulation. Otherwise conventional techniques may be employed to implant the device and its leads. At step 102, during an acute phase or interval following device implant, the pacer/ICD detects HF, PE or other cardiac decompensation events within the patient using one or more detection signals that are relatively insensitive to component encapsulation effects, such as HRV parameters, ventricular ER parameters or other non-impedance-based detection signals or parameters. Herein, the acute phase is generally regarded as the interval between device implant and the point in time when components used for detecting impedance have been properly encapsulated by mature tissues. This is often deemed to take about forty-five days. However, as will be explained in greater detail below, different components may be encapsulated sooner, or in some cases, later than this forty-five day interval. Techniques for detecting the end of acute phase for particular components are described below.

At step 104, following the post-implant acute interval, the pacer/ICD detects possible HF, PE other cardiac decompensation events within the patient using one or more detection signals that are relatively more sensitive to component encapsulation effects, such as transthoracic impedance (PE) signals or intracardiac impedance (CI) signals. Additionally, as will be described, these impedance signals can be supplemented with non-impedance-based signals of the type used during the acute phase so as to improve the specificity and reliability of event detection.

At step 106, based on the detection of any cardiac decompensation events within the patient, the pacer/ICD generates warnings, records diagnostics, titrates medications and/or controls other forms of therapy, as already mentioned.

Figure 3:
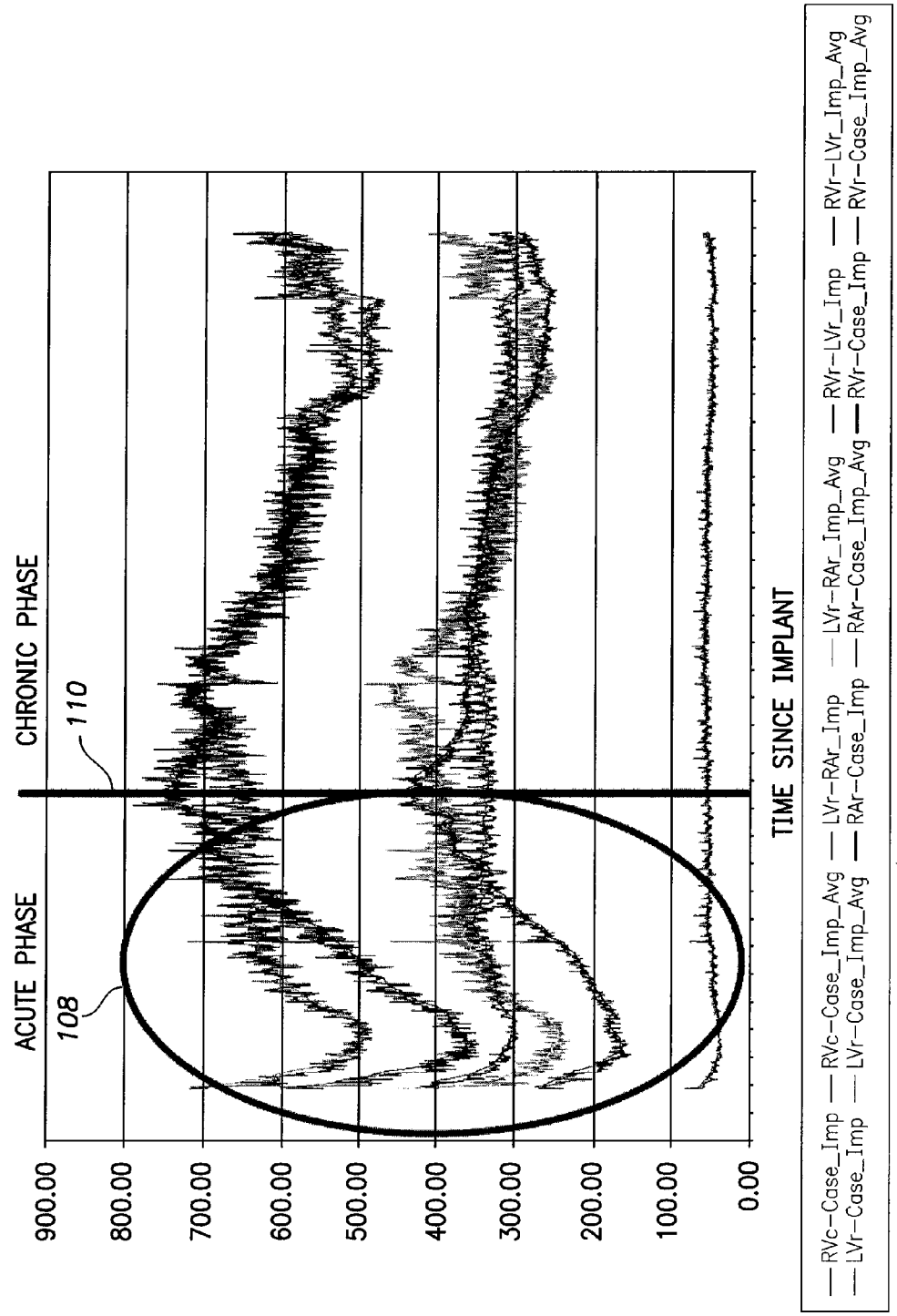
FIG. 3 provides an exemplary graph illustrating changes in various impedance vectors occurring during the acute phase that might otherwise prevent the detection of HF/PE during the acute interval without the techniques of FIG. 2.

FIG. 3 provides an exemplary graph 108 illustrating changes in various transthoracic (i.e. PE) impedance vectors occurring during the post-implant acute phase 108, which may end about forty-five days after implant, as indicated by vertical line 110. As can be seen, during the acute phase, the impedance signals vary significantly. During the subsequent chronic phase, the signals are much more stable. Note that, in this example, even during the chronic phase, some of the transthoracic impedance signals decrease over time, indicative of a possible increase in pulmonary congestion in this particular patient or other physiologic changes. Such increases in pulmonary congestion may be due to pneumonia. Other factors that may affect thoracic impedance are blood/fluid partitioning (i.e., the amount of blood in arteries versus veins, or the amount of plasma in blood versus that in the interstitial), the osmolarity of plasma and interstitial fluids (the balance of which may be affected by drugs, diet, or other conditions), or geometric factors (e.g. if the patient loses weight, the device can may be closer to the leads than before).

Figure 4:
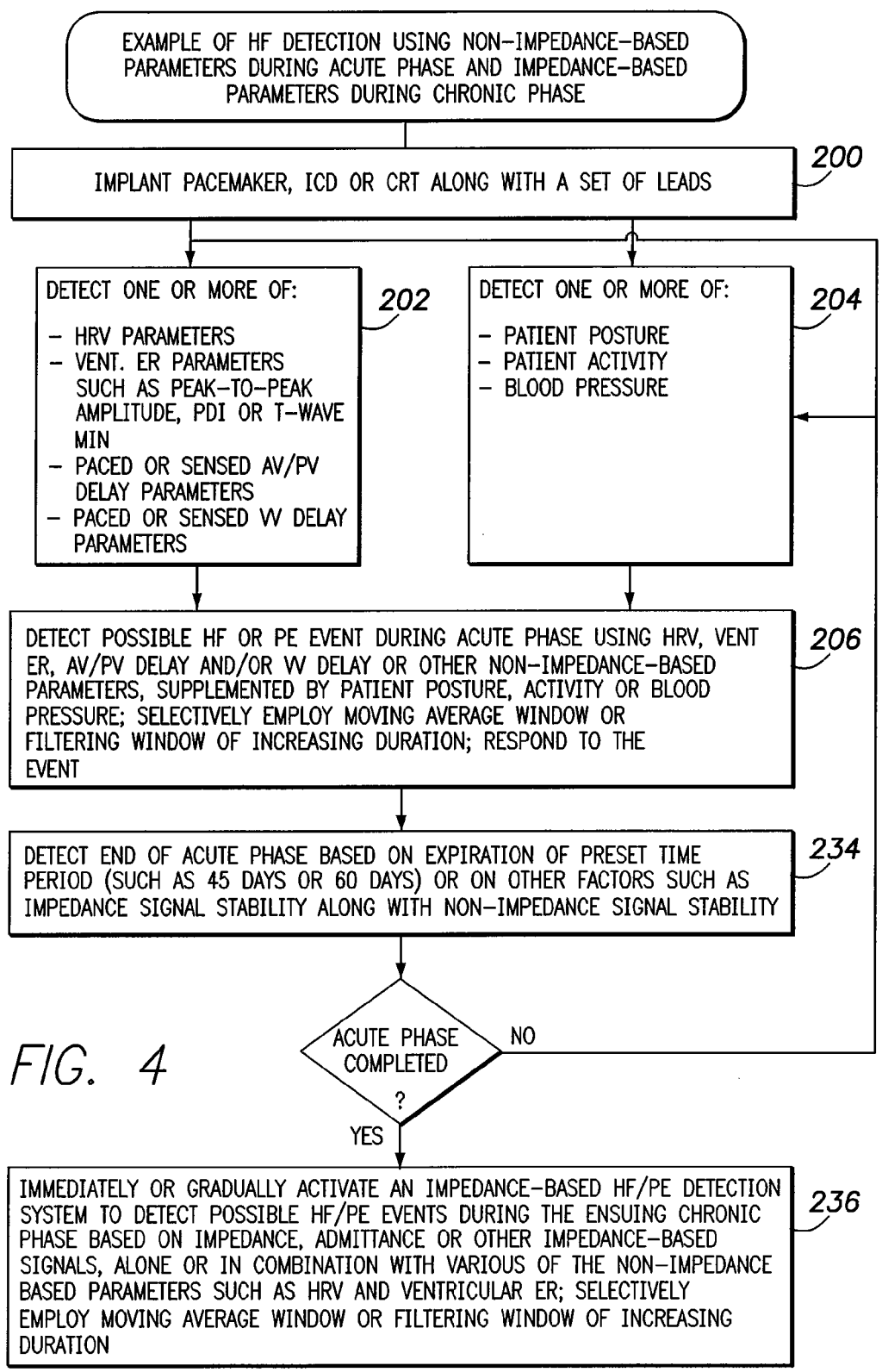
FIG. 4 illustrates an exemplary embodiment of the technique of FIG. 2 wherein HRV, ventricular ER and other non-impedance-based parameters are used to detect HF/PE during the acute phase.

FIG. 4 provides a detailed example of the general technique of FIG. 2 wherein HRV, ventricular ER and other non-impedance-based parameters are used to detect HF/PE during the acute phase. Beginning at step 200, the pacer/ICD is implanted along with its leads. At step 202, the device detects one or more non-impedance-based parameters such as: HRV parameters; ventricular ER parameters; paced or sensed AV/PV delay parameters; and paced or sensed VV delay parameters. Exemplary AV and VV features that can be employed are sensed AV delay, paced AV delay, LV paced RV sense delay, and RV paced LV sense delay. Insofar as AV/PV delay parameters are concerned, it is noted that, advantageously, the AV delay (versus the PV delay) may not require correction for rate dependence since tests can be run at a fixed heart rate (A pacing). However, PV parameters including PV delay or PV delay variability (more strictly speaking, PR delay and PR variability) can be used to measure atrioventricular conduction and sympathetic/parasympathetic balance, respectively.

Exemplary ER features that can be used include: a peak-to-peak amplitude during a ventricular paced depolarization window (wherein "paced depolarization" refers to the portion of the paced ER waveform that is analogous to the QRS-complex within intrinsic cardiac beats); a paced depolarization integral (PDI); a maximum slope (or slew rate) during the paced depolarization window; and an ER T-wave minimum (wherein "ER T-wave" refers to the portion of the paced ER waveform that corresponds to repolarization within intrinsic cardiac beats.) U.S. Pat. No. 6,473,647 to Bradley et al. discusses using ER features, especially a change in the ER feature with respect to the progression of heart disease. See, also, U.S. Pat. No. 7,440,804 to Min et al., entitled "System and Method for Measuring Ventricular Evoked Response using an Implantable Medical Device," which discusses analyzing ER features to detect HF, and U.S. Pat. No. 7,430,447, also of Min et al. entitled "Evoked Response and Impedance Measures for Monitoring Heart Failure and Respiration." PDI is discussed in U.S. Pat. No. 5,643,327 to Dawson et al. Otherwise routine experimentation can be used to identify particular ER or AV/PV/VV features or combinations of features to achieve preferred or optimal algorithms for detecting decompensation events.

Insofar as HRV is concerned, U.S. Pat. No. 6,480,733 to Turcott, entitled "Method for Monitoring Heart Failure," discusses the use of HRV in detecting HF. As noted therein, significant excursions in HRV are indicative of HF exacerbation. Particularly effective techniques for measuring and quantifying HRV are described, for example, in U.S. patent application Ser. No. 12/558,385, filed Sep. 11, 2009, of Bharmi et al., entitled "System and Method for use with an Implantable Medical Device for Detecting Stroke based on Physiological and Electrocardiac Indices."

Typically, the various AV/VV and ER parameters, as well as HRV values, are detected within—or are derived from—intracardiac electrogram (IEGM) signals detected using the various electrodes of the leads. Note that these IEGM signals are not significantly affected by encapsulation affects and hence can be reliably used during the acute phase.

At step 204, the device also detects one or more of: patient posture; patient activity; blood pressure, which can be used to corroborate or supplement the signals and parameters detected at step 202. Techniques for detecting patient posture or changes in posture are set forth in U.S. Pat. No. 7,149,579 to Koh et al., entitled "System and Method for Determining Patient Posture Based On 3-D Trajectory Using an Implantable Medical Device". Patient activity can be detected using an activity sensor or activity variance sensor. Any of a variety of techniques can be used to detect blood pressure. Examples are described in U.S. patent application Ser. No. 11/378,604, filed Mar. 16, 2006, of Kroll et al., entitled "System and Method for Detecting Arterial Blood Pressure based on Aortic Electrical Resistance using an Implantable Medical Device."

At step 206, the device detects a possible HF or PE event during the acute phase using HRV, ventricular ER, AV/PV delay and/or VV delay or other non-impedance-based parameters, supplemented by patient posture, activity or blood pressure signals. In this regard, it is known that AV/VV delays and ER features correlate very well with LAP during rapid pacing-induced cardiac decompensation events in canine test subjects. That is, changes in AV/VV delays and ER features correlate with changes in LAP, which correlate with HF and cardiogenic PE. Hence, changes in AV/VV delays can be used to detect an indication of HF and cardiogenic PE. Also, at step 206, the device responds to the detected decompensation event by, as already explained, generating warnings, titrating medications, delivering therapy, etc. Note also that the device might employ filtering windows or moving average windows to collect and process the non-impedance-based parameters. The duration of these windows can begin at one length and then increase as the acute phase proceeds. For example, an averaging window might be set initially to five days (so as to permit HF detection beginning only five days after implant) and then might expand up to fourteen days as more data is collected. In particular, a system of graded alerts or graded thresholds may be applied during the period with shortened windows. For example, since a "detection" with only five days of data may not be as specific as a detection with fourteen days of data, the alert may be worded more softly, or alternately the threshold to issue an alert or therapy based on only five days would be higher than that to issue alert/therapy based on a longer period.

Figure 5:
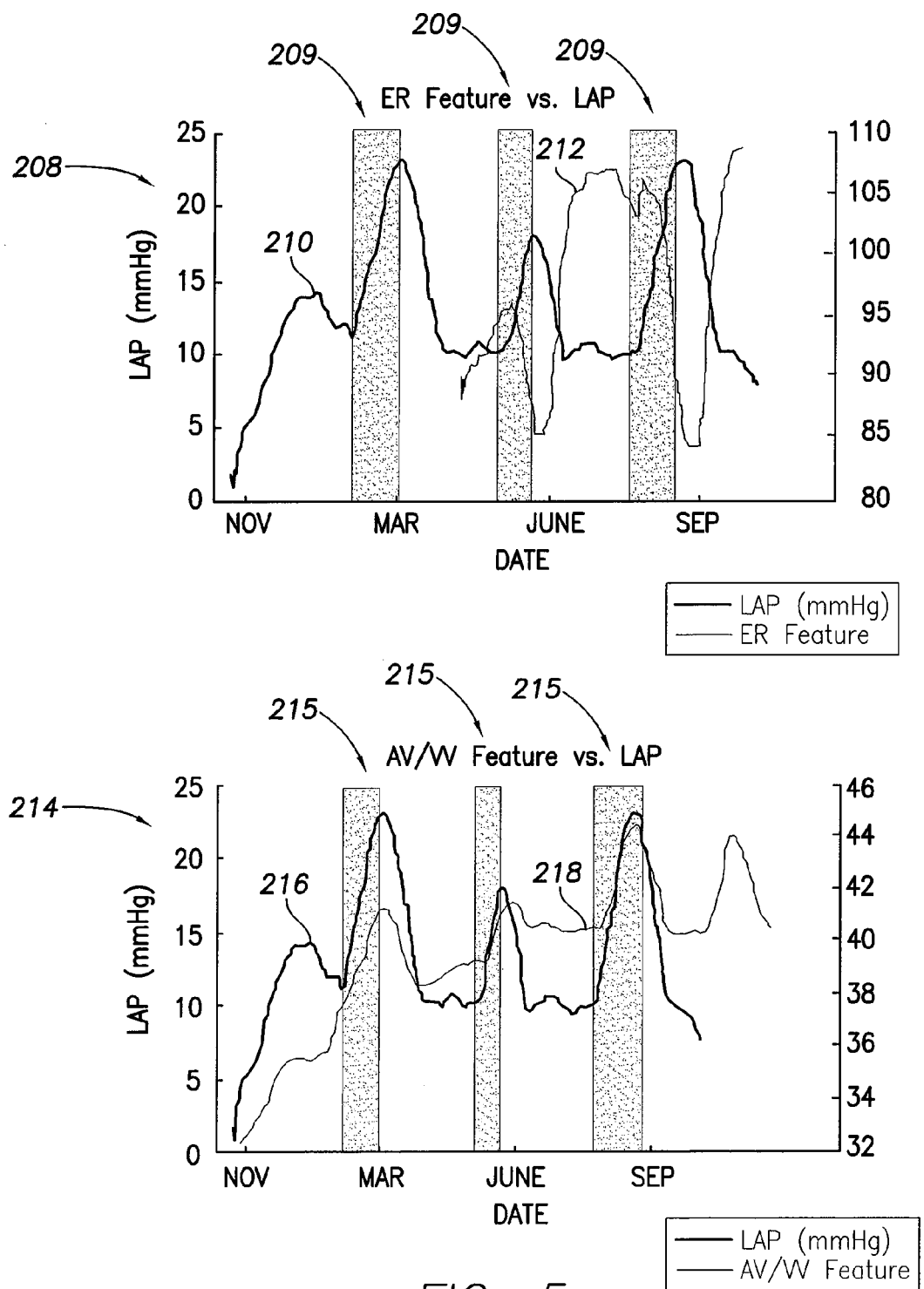
FIG. 5 includes exemplary graphs illustrating changes in ventricular ER and AV/PV delays that can be exploited by the technique of FIG. 4 to detect HF/PE.

FIG. 5 illustrates ER and AV/VV measurements. More specifically, graph 208 illustrates a correlation (inverse, in this case) between an ER feature and LAP. (More specifically, the plotted ER feature is PDI; the units on the vertical axis are mV*ms.) Three rounds of rapid pacing were performed at times 209 to induce decompensation events within a canine test subject and corresponding increases in LAP by as much as 20 mmHg. As can be seen, the ER feature 210 is inversely correlated with LAP 212, such that a sharp decrease in ER can be used to indicate a sharp increase in LAP, which is indicative of a cardiac decompensation event. (Note that LAP was not measured throughout the entire duration of the graph and hence there is gap in the LAP data.) Graph 214 illustrates a correlation (direct, in this case) between an AV/VV feature and LAP. (The AV/VV feature plotted relates to the aforementioned AV/VV delays. More specifically, the plotted feature is LV pace to RV sense time, expressed in ms.) Three rounds of rapid pacing were performed at times 215 to induce decompensation events and corresponding increases in LAP. As can be seen, the AV/VV feature 216 is correlated with LAP 218, such that a sharp increase in the AV/VV feature can be used to indicate a sharp increase in LAP, which is indicative of a cardiac decompensation event.

Figure 6:
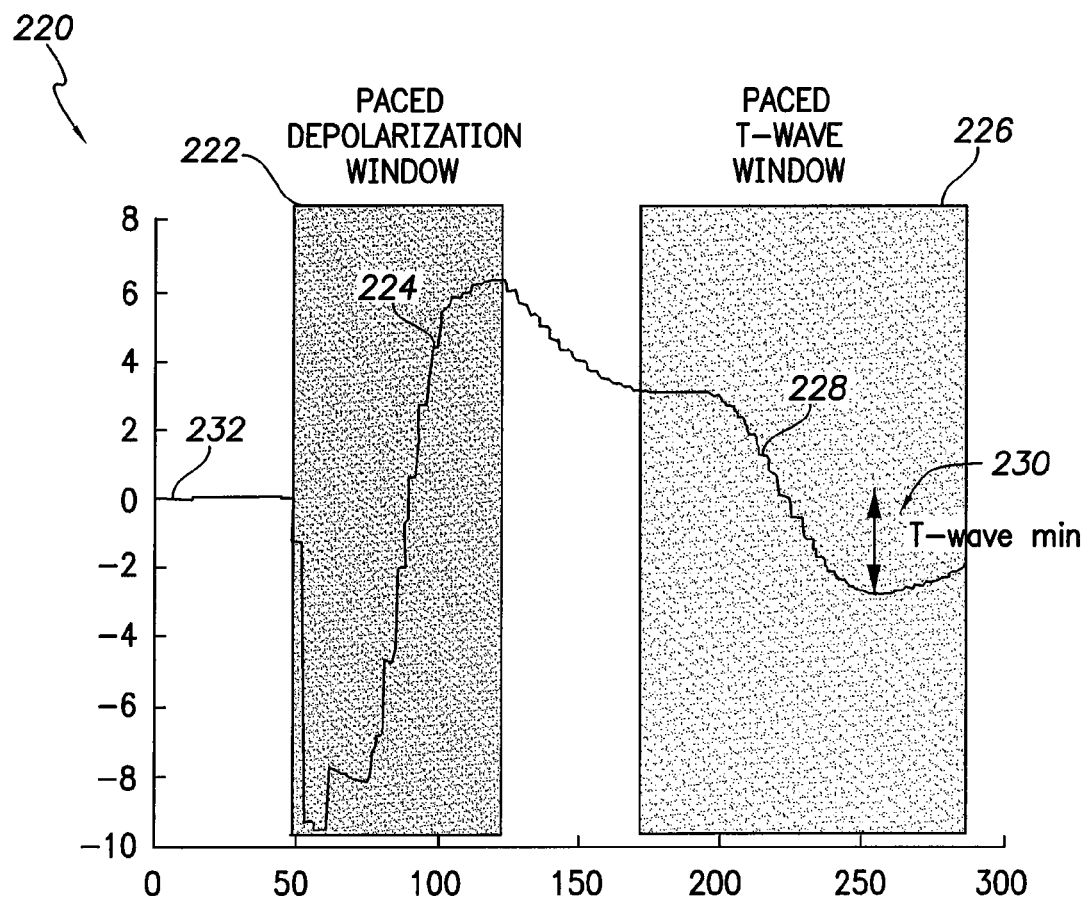
FIG. 6 includes an exemplary graph illustrating an ER T-wave min parameter that can be exploited by the technique of FIG. 4 to detect HF/PE.

FIG. 6 illustrates the ER T-wave min feature (also referred to herein as the "paced T-wave min") that can be used as one of the non-impedance based parameters at step 206 of FIG. 4. More specifically, graph 220 illustrates a paced depolarization window 222 in which a paced depolarization event 224 is detected. The graph also illustrates a paced T-wave window 226 in which an ER T-wave 228 is detected. The ER T-wave minimum 230 is measured with respect to a baseline level 232. Note that U.S. Pat. No. 7,072,715 to Bradley, entitled "Implantable Cardiac Stimulation Device for and Method of Monitoring Progression or Regression of Heart Disease by Monitoring Evoked Response Features" discusses the use of the ER T-wave, particularly T-wave slew rate and T-wave amplitude, for tracking HF. See, also, U.S. Pat. No. 7,676,264 to Pillai et al., entitled "Systems and Methods for use by an Implantable Medical Device for Evaluating Ventricular Dyssynchrony based on T-wave Morphology."

Returning to step 206 of FIG. 4, insofar as supplementing the detection of HF/PE with patient posture, activity or blood pressure, these parameters can be used to help avoid false HF detections that might be triggered by changes in posture or patient activity, including activity triggering increases in blood pressure. That is, if HF is indicated based on the aforementioned non-impedance-based parameters, but that indication coincides with significant changes in posture or activity, then the device preferably collects and analyzes additional data before taking action in response to the HF event. This represents just one possible way to interpret sensor-related changes in the context of additional data on posture and/or activity. An alternative interpretation is to "bin" sensor data such that there are multiple trends stored and updated, corresponding each to one set of posture or activity data. See, generally, U.S. Pat. No. 7,336,999 to Koh, entitled "Means to Check the Validity of Heart Failure Surrogate Parameters from Evoked Response using 3-D Accelerometer Queue."

At step 234, the implanted device detects the end of the acute phase based on the expiration of predetermined time period (such as forty-five days or sixty days) or based on other factors such as impedance signal stability. In one particular example, a sixty-day interval is employed which is based on a forty-five day post-implant moratorium plus a two-week impedance data collection averaging interval. In another example, a forty-five-day interval is employed which is based on a thirty day post-implant moratorium plus a two-week impedance data collection averaging interval. As such, these intervals are merely exemplary and other durations can be selected. Insofar as assessing impedance stability is concerned, the device tracks changes in impedance occurring during the acute phase (see, again, FIG. 3) to detect when those changes stabilize (by, for example, comparing a parameter representative of impedance variation against a threshold indicative of stabilization.) Note that the non-impedance-based parameters can be used to corroborate or supplement the determination that impedance signals have stabilized. For example, referring again to FIG. 3, about thirty days after implant, several of the transthoracic (PE) impedance vectors appear to level off. If the impedance values are deemed to be level by the device, and the ER, AV/VV, and HRV features indicate that the patient is stable during the same period, the device can then conclude that the corresponding electrodes have matured so that impedance-based HF/PE detection can be invoked. On the other hand, if the impedance vectors appear to be level but the non-impedance features indicate that the patient is transitioning (e.g. HF worsening) then the "apparent" stability of impedance vectors are deemed to be false and a full sixty days should be allowed for maturation (or forty-five days in examples where a shorter moratorium is used.) Thus, an apparent stabilization of PE/CI signals that is corroborated by stable ER, AV/VV, HRV, and/or other sensors can enable early termination of the maturation period and entry into the full impedance-based HF/PE monitoring algorithm. Additionally or alternatively, the device can exploit the techniques discussed below with reference to FIGS. 7-14 to detect the maturation of encapsulation. Note also that there can be fluctuations on the impedance trend depending upon how frequently data is collected. For FIG. 3, data was collected every two hours. In contrast, FIG. 8 (discussed below) illustrates impedance data collected only once a day and hence the data of FIG. 8 appears more stable.

Continuing with FIG. 4, assuming the patient is still within the acute phase, processing returns after step 234 to steps 202 and 204 for further acute interval processing. Once the acute phase has ended, processing continues to step 236 wherein the device immediately or gradually activates its impedance-based HF/PE detection systems to detect possible HF/PE events during the ensuing chronic phase based on impedance. Note that, rather than detecting impedance, other related electrical signals or parameters can instead be exploited, such as admittance, conductance, immittance or their equivalents. Generally, herein, "impedance signals" or "impedance parameters" broadly encompasses impedance and/or any of these electrical equivalents and those skilled in the art can readily convert one such parameter into another. Note also that the impedance-based detection of step 236 may be performed either alone or in combination with various of the non-impedance based parameters already discussed, such as HRV and ventricular ER. That is, non-impedance-based detection parameters can be used to corroborate or supplement any HF/PE detection made based on impedance signals.

The impedance-based HF/PE detection performed at step 236 can exploit techniques of the various patent documents cited above, such as those by Bornzin et al., Min et al, Panescu et al., and Wenzel et al. See, also, techniques described in U.S. patent application Ser. No. 11/559,235, entitled "System and Method for Estimating Cardiac Pressure Using Parameters Derived from Impedance Signals Detected by an Implantable Medical Device," and also techniques described in the following applications: U.S. Provisional Patent Application No. 60/787,884 entitled "Tissue Characterization Using Intracardiac Impedances with an Implantable Lead System" and in U.S. patent application Ser. Nos. 11/558,101; 11/557,851; 11/557,870; 11/557,882; and 11/558,088, each entitled "Systems and Methods to Monitor and Treat Heart Failure Conditions."

Insofar as non-impendence-based corroboration is concerned, an HF detection parameter can be generated that combines impedance-based indicators with non-impedance-based indicators for comparison against one or more thresholds indicative of a cardiac decompensation event. See, for example, the graded alerts or graded thresholds discussed above. The relative weights given the impedance-based parameters vs. the non-impedance-based parameters can vary gradually as the acute interval comes to an end. For example, upon completion of the acute phase, the weight applied to impedance-based signals can be gradually increased until reaching some preferred weight for use during the chronic phase. An impedance averaging window or a filtering window can be used that increases in duration up to some preferred length for use during the chronic phase. Note that the particular non-impedance-based parameters used during the chronic phase might differ from those used during the acute phase. Likewise, any particular thresholds used for detecting HF/PE can differ during the chronic phase as compared to the acute phase. Furthermore, thresholds used during the lead maturation or after lead maturation can be manually set by a clinician or other user. In some implementations, these different thresholds are automatically determined by the device. When the device sets the thresholds, they can be fixed thresholds or patient-specific thresholds. Insofar as ER-based corroboration is concerned, see, e.g., U.S. Patent Application 2005/0216067 of Min et al., "System and Method for Predicting a Heart Condition based on Impedance Values using an Implantable Medical Device," which discusses techniques wherein ER features are exploited to corroborate the HF predictions.

Thus, FIGS. 2-6 illustrate exemplary techniques for detecting cardiac decompensation events during the initial acute phase using non-impedance based parameters. In the following section, techniques for early activation of impedance-based detection systems are described.

Maturation-Based Activation of Impedance-Based HF/PE Detection Systems

Figure 7:
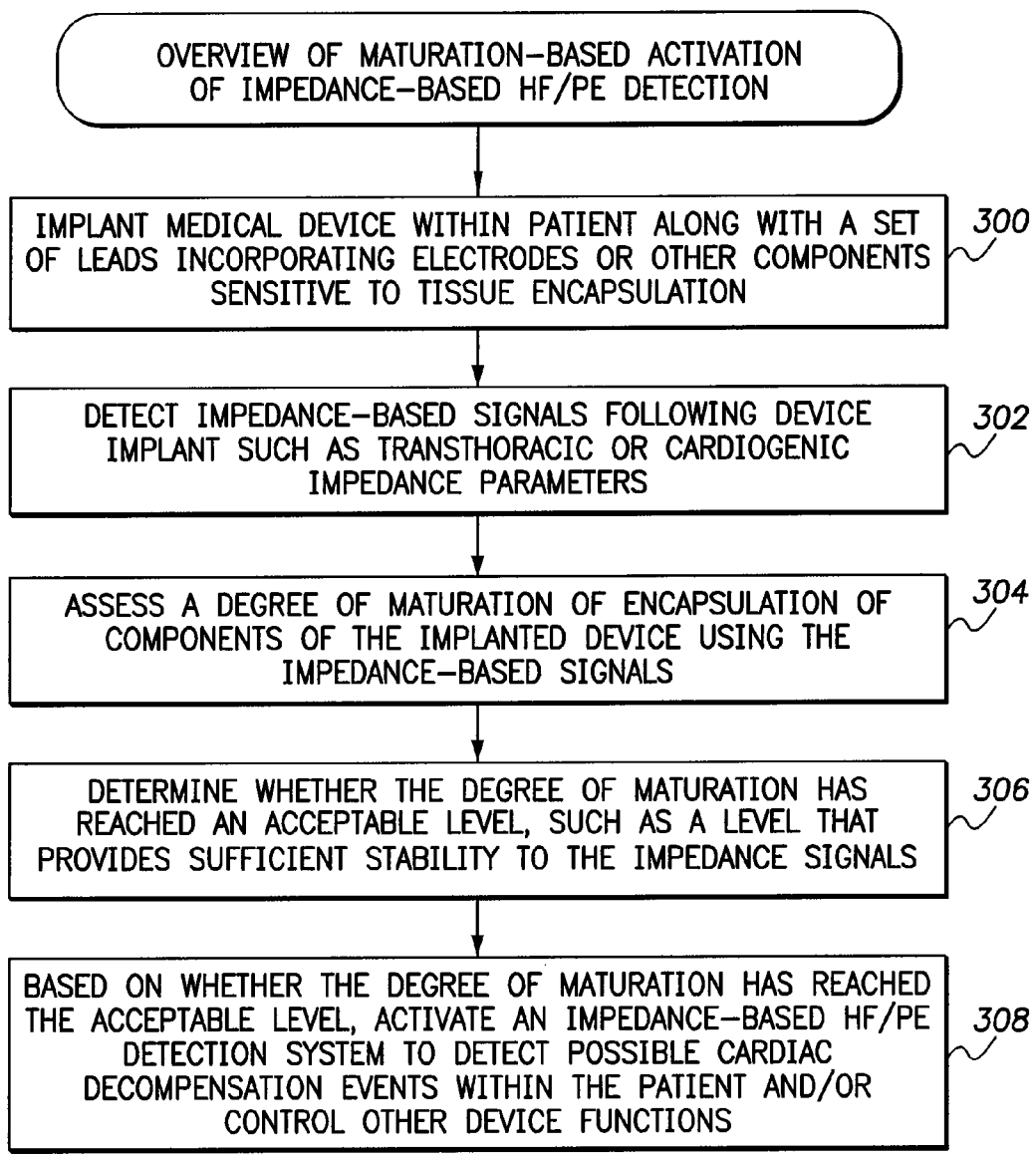
FIG. 7 provides an overview of a method performed by the system of FIG. 1 for activating an impedance-based HF/PE detection system based on the degree of maturation of component encapsulation.

FIG. 7 summarizes techniques for activating impedance-based HF/PE detection systems based on a degree of maturation of component encapsulation as detected by the implanted device. Beginning at step 300, the pacer/ICD is implanted within a patient along with a set of leads that incorporate electrodes or other components sensitive to tissue encapsulation. At step 302, the device detects impedance-based signals following implant of the device such as transthoracic (PE) or cardiogenic impedance (CI) parameters. At step 304, the device assesses the degree of maturation of encapsulation of components of the implanted device using the impedance-based signals. Exemplary techniques will be described in detail below that assess the type of tissue surrounding particular electrodes and the thickness thereof. At step 306, the device determines whether the degree of maturation has reached an acceptable level, such as a level ensuring stability of the impedance signals. Then, at step 308, based on whether the degree of maturation has reached the acceptable level, the device controls or activates its impedance-based HF/PE detection systems to detect possible cardiac decompensation events within the patient and/or to control other device functions in response thereto. Prior to this point in time, the device can instead use the aforementioned non-impedance-based parameters to detect HF/PE. Any of the various transitioning techniques discussed above, where relative weights are adjusted or where the durations of filtering windows are selectively varied, can be used as well, to transition from one detection technique to another. Insofar as controlling device functions is concerned, it should be understood that any function that the pacer/ICD can perform or control, alone or in combination with other devices, is a "device function." The term "controlling" broadly encompasses any of a variety of control functions, such as activating device components/procedures, deactivating device components/procedures, adjusting device components/procedures, etc.

Figure 8:
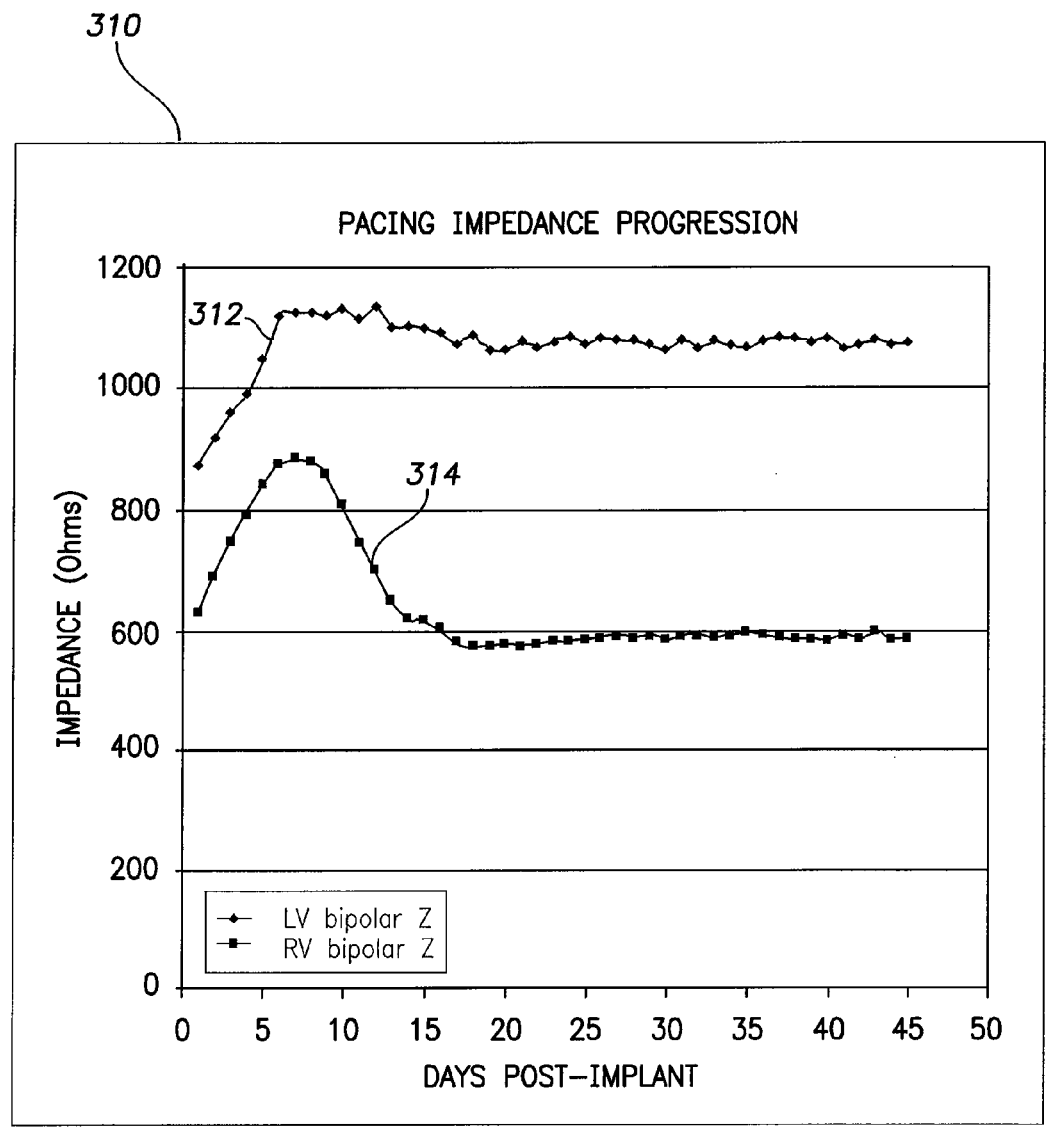
FIG. 8 includes an exemplary graph illustrating changes in the magnitude of impedance signals following device implant that can be exploited by the technique of FIG. 7 to detect maturation of encapsulation based on impedance stability.

FIG. 8 provides an exemplary graph 310 illustrating changes in transthoracic (i.e. PE) impedance vectors occurring post-implant, particularly an LV bipolar impedance vector 312 and an RV bipolar impedance vector 324. In this example, during the first ten or so days following implant, the LV bipolar impedance changes significantly, then stabilizes. The RV bipolar impedance stabilizes after about twenty days. As such, both stabilize well in advance of the typical forty-five day impedance-detection moratorium discussed above. With the technique of FIG. 7, this early stabilization is detected to permit early use of impedance-based HF/PE detection systems.

Figure 9:
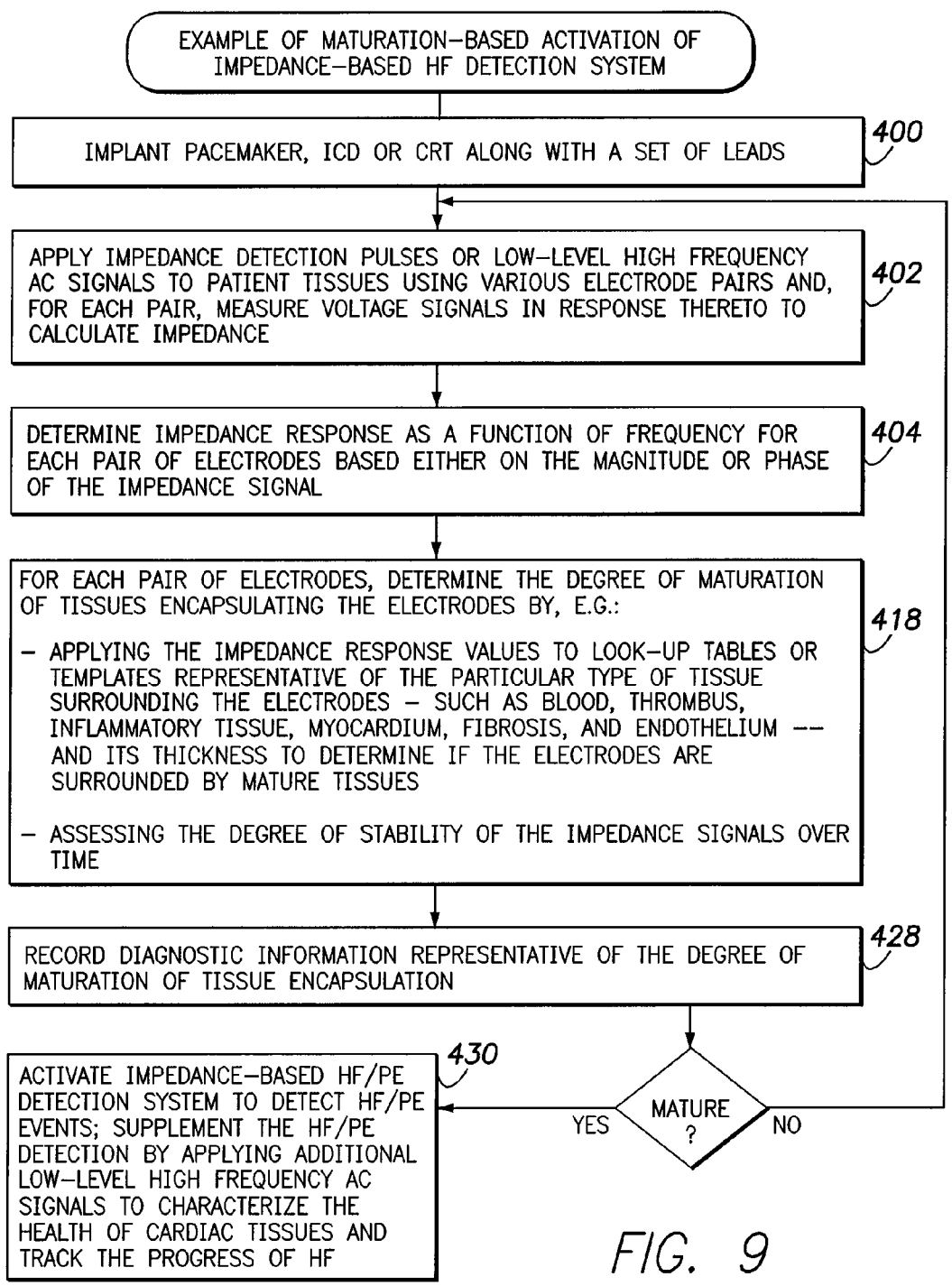
FIG. 9 illustrates an exemplary embodiment of the technique of FIG. 7 wherein frequency response used to determine the degree of maturation of electrode pairs.

FIG. 9 provides an example of the general technique of FIG. 7 wherein frequency response is used to assess the particular type of tissue surrounding electrodes, as well as its thickness. Beginning at step 400, the pacemaker, ICD, CRT or other medical device is implanted along with its leads. At step 402, the device applies impedance detection pulses or low-level high frequency AC currents to patient tissues using various electrode pairs and, for each pair, measures voltage signals in response thereto to calculate impedance.

A particularly effective tri-phasic impedance detection pulse for use in detecting impedance is described in U.S. patent application Ser. No. 11/558,194 of Panescu at al., filed Nov. 9, 2006, entitled "Closed-Loop Adaptive Adjustment of Pacing Therapy based on Cardiogenic Impedance Signals Detected by an Implantable Medical Device." The tri-phasic waveform is a frequency-rich, low energy waveform that provides a net-zero charge and a net-zero voltage. However, other impedance detection pulses or waveforms may instead be exploited. Insofar as the low-level, high-frequency AC current is concerned, this current is driven across an electrode pair and then the voltage across the same or another electrode pair is measured to determine an impedance value. For example, 16 Hz for PE, 128 Hz for CI measurements. In general, the impedance value will have real and imaginary parts, which can be considered mathematically as an amplitude and phase components. Several frequencies of current are driven (at the same or different times) and the resultant voltages are measured to generate plots of impedance (amplitude or phase) versus frequency (wherein the plots are stored internally within the memory systems of the device using suitable data representations.)

To distinguish between different possible tissues, a wide frequency range should be tested, for example from direct current (DC) or 0.1 Hz up to 10 MHz-100 MHz. This range need not be sampled completely nor uniformly, and in fact it may be advantageous to take only 1 or 2 frequency samples in each decade (i.e. logarithmic sampling). Alternately, it may be possible to drive current such as white noise or pink noise, and measure the spectral response. Insofar as the amplitude is concerned, a typical requirement is that current density remains below the capture threshold of cardiac tissue (or muscle tissue in the device pocket). For example, in a typical implantable system, 1-10 uA should not capture cardiac tissue in the range approx >0.1 kHz The impedance value measured using a given pair of electrodes is a pair-based or vector-based impedance value that reflects the impedances associated with the pair of electrodes. As noted above, it is now believed that the majority of the impedance characteristics occur within about one centimeter of measuring electrodes. That is, the measured impedance is dominated by the effects of near-field tissues rather than far-field tissues. As such, the impedance measured using a particular pair of electrodes represents the impedance near the first electrode of the pair combined with the impedance near the second electrode of the pair. Typically, about 80%-95% of the signal is within the near-field of either electrode, with the remaining 5-20% representing everything in between (blood, tissue, interstitial fluid, air, etc.) Note also that, the impact of cathode is typically much more important than anode. For example, a transthoracic (PE) impedance signal measured between the LV tip and the device housing primarily represents a combination of the impedance near the LV tip and the impedance near the device itself, with comparatively little contribution from the far-field between the two electrodes. Note though, that the far-field signal still has small contribution. Assuming that near-field signals (such as the LVtip and Can local impedance values) do not change significantly during pulmonary edema, the small change in far-field then becomes the major differentiator. Hence, despite the relatively modest far-field contribution, pulmonary fluid content can typically be detected based on changes of ~10% (e.g., a 50 Ohm drop on a 500 Ohm signal is certainly detectable by the device impedance measurement circuitry). If the tissues around either of the two electrodes of the pair have not yet matured, then the pair typically cannot be used to measure impedance for the purposes of HF/PE detection. That is, it is not sufficient that just one of the electrodes of the pair has been encapsulated by mature tissues. Both of the electrodes of the measuring pair should be properly encapsulated. Note also that, if the device measures several electrical vectors, it is typically feasible to discern the individual effects of each electrode using near-field-based techniques.

Techniques have been developed for determining the near-field impedance associated with an individual electrode, i.e. for isolating the impedance associated with a particular electrode rather than a pair of electrodes. See, the near field-based impedance techniques described in U.S. patent application Ser. No. 12/853,130, filed Aug. 9, 2010, of Gutfinger et al., entitled "Near Field-based Systems and Methods for Assessing Impedance and Admittance for use with an Implantable Medical Device." These near field techniques might be useful in connection with the present invention to identify encapsulating tissues on an electrode-by-electrode basis. However, unless otherwise noted, the impedance measurements employed by the techniques described herein are vector-based or pair-based impedances, which reflect a combination of the impedances of the two electrodes of the voltage measuring pair.

At step 404, the device determines the impedance response as a function of frequency for each pair of electrodes used to measure impedance based either on the magnitude or the phase of the impedance signal.

Figure 10:
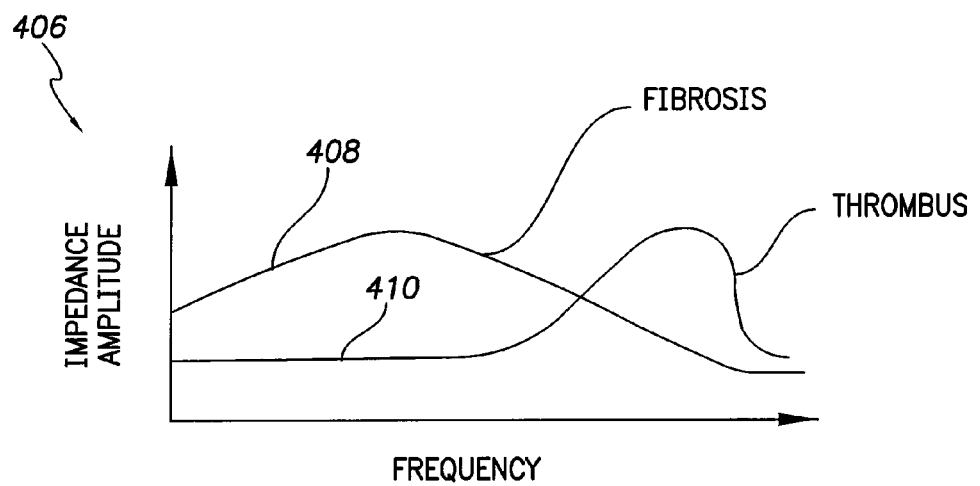
FIG. 10 includes exemplary graphs illustrating changes in impedance amplitude and phase as a function of frequency for fibrotic and thrombotic tissues that can be exploited by the technique of FIG. 9.
Figure 10:
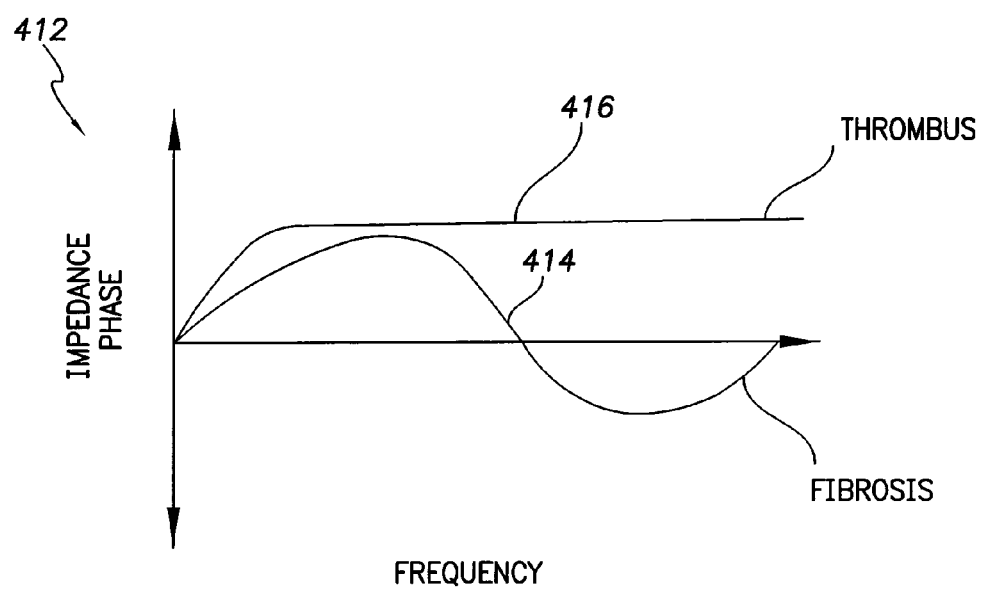

FIG. 10 illustrates exemplary impedance frequency response curves. At first graph 406 provides two curves of impedance amplitude as a function of frequency corresponding to different tissues encapsulating one or both electrodes of the measuring pair. Curve 408 represents the amplitude-frequency response in the presence of fibrotic tissue. Curve 410 represents the amplitude-frequency response in the presence of thrombotic tissue. As can be seen, the frequency response is quite different, permitting the device to distinguish the two types of encapsulating tissue. At second graph 412 provides two curves of impedance phase as a function of frequency. Curve 414 represents the phase-frequency response in the presence of fibrotic tissue. Curve 416 represents the phase-frequency response in the presence of thrombotic tissue. Again, the frequency response is quite different. See, U.S. patent application Ser. No. 11/844,131 of Rosenberg et al., filed Aug. 23, 2007, entitled "System and Method for In Vivo Sensor Recalibration", which describes the use of similar impedance measurements at various frequencies for the purpose of recalibrating sensors.

The frequency response curves of FIG. 10 represent just a few examples that illustrate the differences in impedance response caused by different encapsulating tissues. Additional frequency response curves can be generated without undue experimentation for other types of tissues expected to encapsulate implantable electrodes during the maturation process, particularly blood, inflammatory tissue, myocardium and endothelium. Lookup tables or templates are then stored within the memory of device so that the device can compare measured frequency response curves with the stored data to identify the type of data encapsulating the measuring electrodes. This is performed in the next step of FIG. 9.

Note that, in some cases, two or more different types of tissues might encapsulate particular electrodes and so frequency-response curves can be generated that account for the presence of a combination of different tissues by, for example, using look-up tables. Alternatively, template-matching may be employed for the frequency response curves, such that only the tissue type most closely resembling the measured response is identified. Yet another option is to employ a fuzzy-logic system that identifies the actual (probabilistic) contribution of each encapsulating tissue type.

Likewise, in some cases, different types of tissues might encapsulate the two electrodes of a given electrode pair (e.g. the LV tip electrode might be encapsulated by one type of tissue, whereas the device housing might be encapsulated by another type of tissue) and so frequency-response curves are also preferably generated that account for such combinations. See, again, the near-field techniques of Gutfinger et al. cited above that can be used to isolate the contributions of individual electrodes. In some cases, due to the presence of too many different types of encapsulating tissues, or for other reasons, it might not be feasible for the device to identify the particular tissues associated with a given pair of electrodes. In such circumstances, alternative techniques are used to assess the maturity of the encapsulating tissue, such as the impedance stabilization techniques discussed below.

Note that frequency-response curves can be generated using either impedance detection pulses or low-level high frequency AC currents or some combination thereof. For example, the "frequency-rich triphasic pulse" may be tuned such that a small number of different pulses of the same family cover the entire frequency range of interest. In the case of impedance pulses—so long as the pulse is sufficiently rich in frequencies—a suitable frequency response can be measured. See, e.g., the frequency-rich tri-phasic pulse mentioned above.

Returning to FIG. 9, at step 418, for each pair of electrodes to be assessed, the device determines the degree of maturation of tissues encapsulating the electrodes based on the impedance response by, e.g., applying the impedance response values obtained at step 404 to look-up tables or templates representative of the particular type(s) of tissue(s) surrounding the electrodes—such as blood, thrombus, inflammatory tissue, myocardium, fibrosis, and endothelium—to determine if the electrodes are surrounded by mature tissues. In one example, if the tissue surrounding an electrode pair is found to be inflammatory tissue, then encapsulation has not yet matured. Conversely, if the tissue surrounding the electrode pair is found to be fibrotic tissue, then encapsulation is deemed to have matured. The particular type of tissue that is deemed to be mature tissue can vary depending upon electrode type and location. For a ring electrode for implant within one of the chambers of the heart or the coronary sinus, blood may be regarded as a mature "encapsulating" tissue. For an active-fixation tip electrode for implant into the myocardium, myocardial tissue may be regarded as immature tissue since scar tissue has not yet formed around the electrode. Additionally, at step 418, the device can assess the thickness of at least some types of tissues based on the amplitude of the measured impedance.

Figure 11:
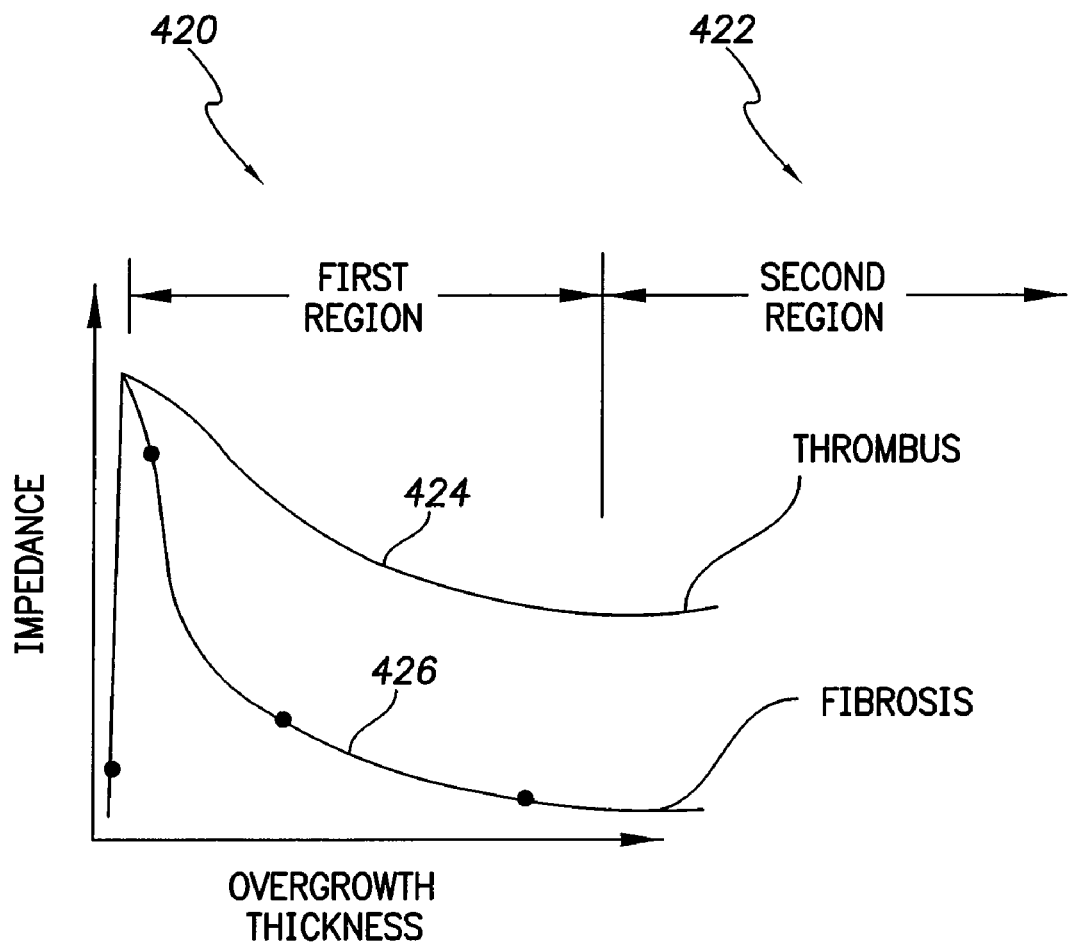
FIG. 11 includes exemplary graphs illustrating changes in impedance as a function of overgrowth thickness for fibrotic and thrombotic tissues that can be exploited by the technique of FIG. 9.

FIG. 11 illustrates impedance as a function of overgrowth thickness for thrombus and fibrosis. In a first region 420 of thickness, impedance drops with increasing thickness. In a second region 422 of thickness, impedance does not change significantly. In the first region, impedance begins dropping as thickness increases due to changes in the distance between the current source and the interface between encapsulating tissue with blood. In the second region, the thickness of the encapsulating tissue is enough such that the tissue-blood interface has little to no effect on further impedance drops. This is the criterion for a fully matured lead, at which point impedance-based HF/PE diagnostics may be activated without significant risk of false detections. Note also that, in both regions, the type of tissue also affects the impedance. Curve 424 corresponds to thrombus. Curve 426 corresponds to fibrosis. As such, based on the measured impedance and the known tissue type (determined from the frequency response), the device can assess the thickness of growth currently surrounding the electrodes. The thickness can be used to assess maturity. For example, for a given electrode and for a given type of encapsulating tissue, a thickness "region" threshold can be defined. If the thickness is found to exceed that threshold, the encapsulation is deemed to be mature, since further increases in thickness are not likely to affect impedance. Note that, even if the tissue type is not known, using the time course of impedance changes the device can match a template of a curve such as 424 or 426. Alternatively, the device can set a threshold for the slope of the curve, such that when the local impedance-versus-time curve is "flat enough" then the device can confidently conclude that the overgrowth thickness has reached a plateau.

Returning to FIG. 9, at step 418, the device additionally or alternatively assesses the degree of stability of the impedance signals over time so as to determine the degree of maturity. In one example, a bipolar pacing lead impedance is measured daily, such as LVtip-LVring and RVtip-RVcoil bipolar impedances. The average over several days is stored as a trend to determine stability. Note that the same bipolar pacing impedance vectors may be used to help determine the stability of one or more transthoracic (PE) impedance vectors. For example, the pacing impedance for the RV bipolar can contribute to determination of stability for RV-LV vector, RA-RV vector, RV-Case vector, etc.

Various specific mathematical methods can be used to determine stabilization. For example, comparison of current values or a short term averages with a long-term average can be used to indicate a stable period if the current value does not differ from the average value, or it can indicate that the electrode is still in maturation period if the current value does differ substantially from the average. As another example, the change from a previous measurement to a current measurement can be compared with the standard deviation of all previous measurements (or those during a pre-specified backward-looking window) and if the change is small relative to the standard deviation then a stable period is indicated. Conversely, if the change is large relative to the standard deviation then an unstable maturation period is indicated. Other methods of determining stability are known as well. Such methods may be applied not only to the bipolar pacing impedance, but also to the transthoracic (PE) impedance signals themselves. In particular, if only one or two signals mature differently than the others, there is higher probability that this is due to differing tissue/lead maturation rather than an acute change in only one of the six measured PE vectors.

The stabilization determined by these methods can be used to flag impedance vectors that are ready for use so the vectors can be used as they become ready. For example, some devices record six PE impedance vectors but only rely on two (RVcoil-Case, LVring-Case) for calculation of a Pulmonary Fluid Index. It may be advantageous to have a modified Fluid Index during the stabilization period that uses any or all of the six (or other) impedance vectors (that have matured) until the time when both RVcoil-Case and LVring-Case have matured, at which point the conventional Fluid Index derived from those particular vectors is used.

At step 428, having determined the degree of maturation of encapsulating tissues, the device then records diagnostic information representative of the degree of maturation of tissue encapsulation, including tissue type, overgrowth thickness, and an indication of whether a given electrode pair can be used for measuring impedance for the purposes of HF/PE detection.

If the encapsulating tissue for the electrodes to be used for impedance-based HF/PE detection is not yet mature, processing returns to step 402 for further monitoring. Steps 402-428 of the figure may be performed periodically or on demand. For example, serial measurements are taken over hours, days, or up to a few weeks and the resulting trend is used to identify the onset of stability. Once at least one pair of electrodes (that are sufficient for impedance-based HF/PE detection) have matured, processing proceeds to step 430.

At step 430, the device then activates its impedance-based HF/PE detection systems to detect HF/PE events or other cardiac decompensation events using any or all stable electrode pairs. Additionally, even though impedance-based HF/PE detection systems have been activated that rely on impedance detection pulses, the device can still apply additional low-level high frequency AC signals to supplement the HF/PE detection by, for example, using those signals to characterize the health of cardiac tissues. In this regard, it is likely that healthy tissue and heart failure tissue will have different characteristic responses to AC impedance. For example, it is known that ischemic myocardium has a different response than non-ischemic myocardium; myocardial remodeling during heart failure progression includes replacing some myocytes with fibrosis, even in the absence of ischemia. Thus, in at least some embodiments, the device utilizes the characteristic impedance response (amplitude and phase) of the tissue to bipolar AC impedance to track HF progression or otherwise contribute to a diagnosis of HF. This may be performed independently or in conjunction with the impedance measured via impedance detection pulses.

Thus, FIGS. 7-11 illustrate various techniques for assessing the degree of maturity of electrodes or electrode pairs and for selectively activating impedance-based HF/PE detection systems. These techniques are applicable to a wide variety of leads and electrode pairs. In the following, a specific example is described wherein the technique is applied to the device housing.

Figure 12:
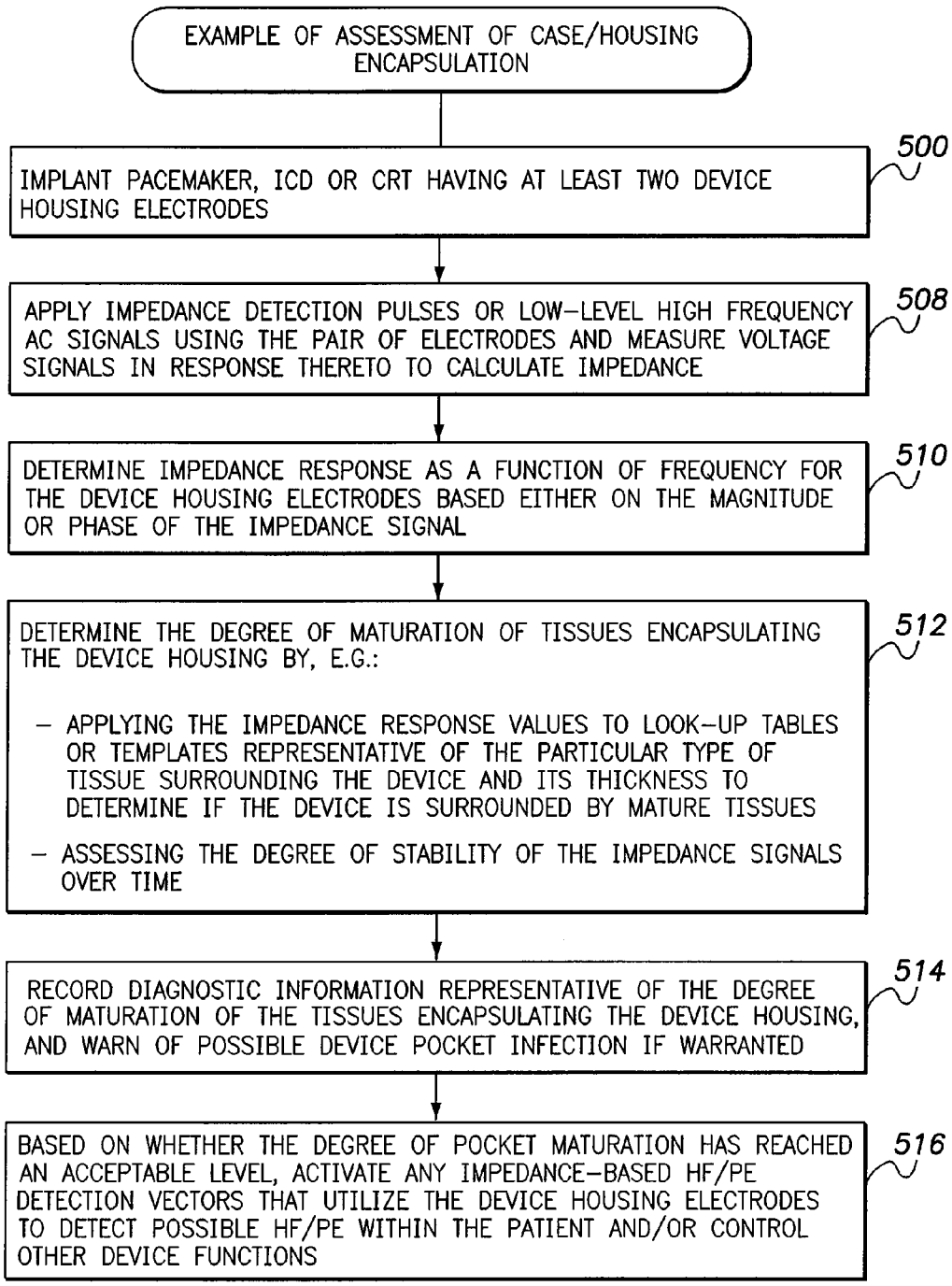
FIG. 12 illustrates an exemplary embodiment of the technique of FIG. 7 wherein the maturation of the device pocket is assessed based on impedance as measured by a pair of device housing electrodes.
Figure 13:
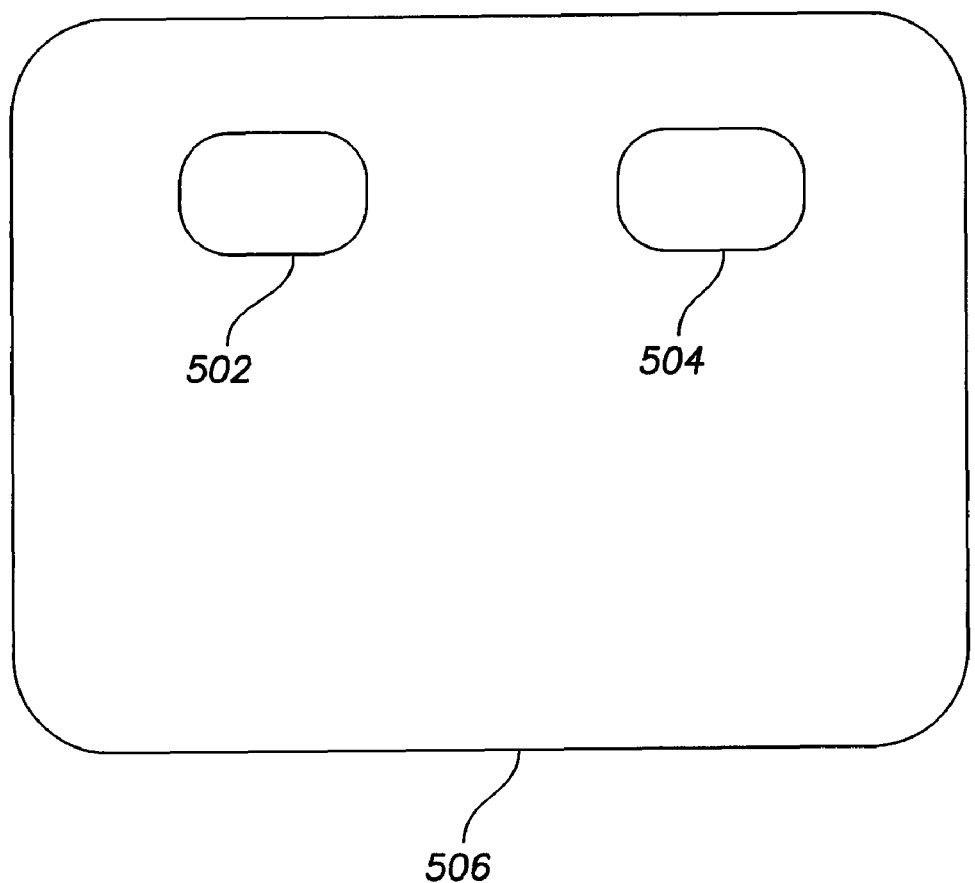
FIG. 13 illustrates a pair of device housing "can" electrodes that can be exploited using the technique of FIG. 12 to assess the maturation of the device pocket.
Figure 14:
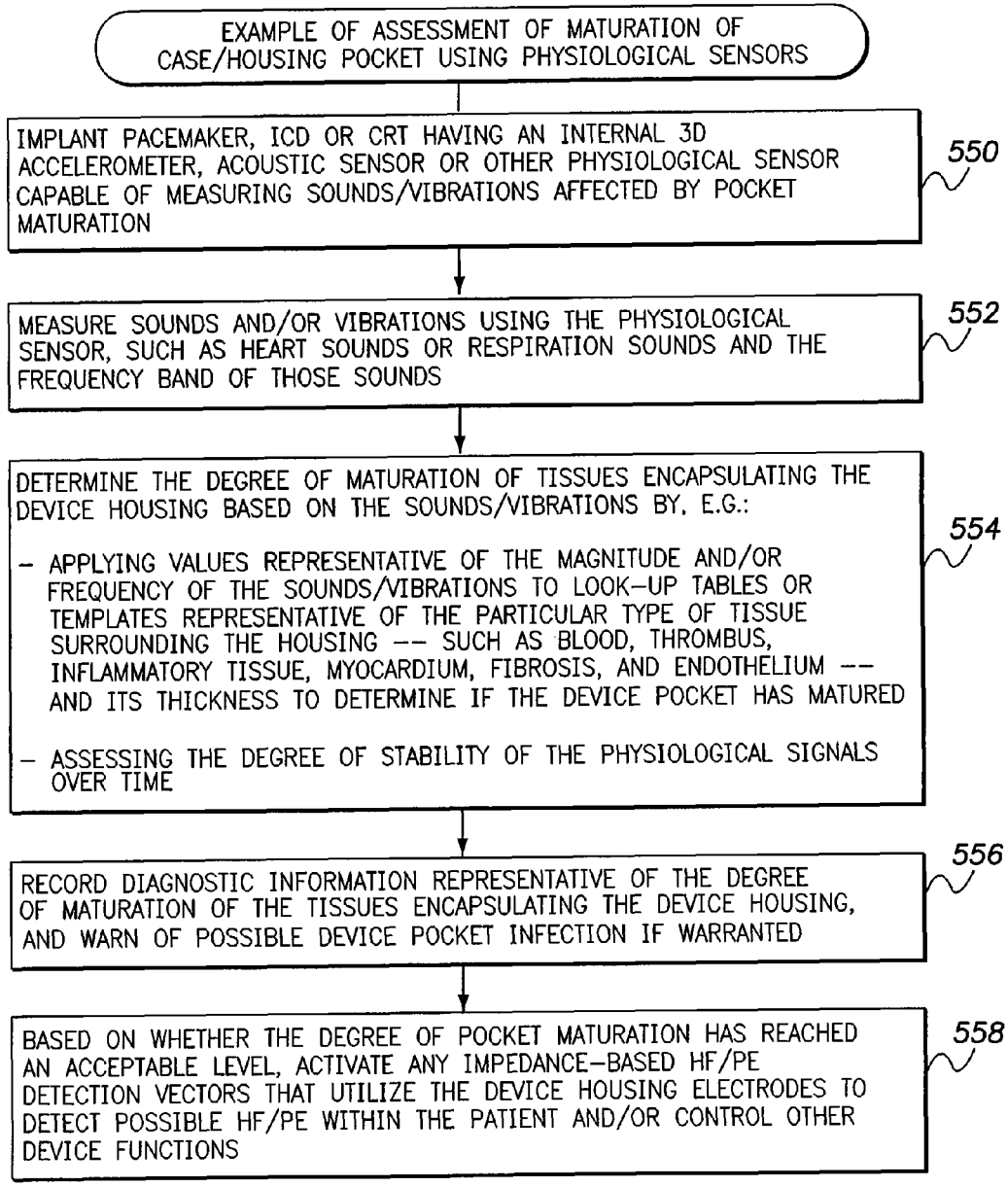
FIG. 14 illustrates an exemplary embodiment of the technique of FIG. 7 wherein the maturation of the device pocket is assessed based on physiological sensor signals such as heart sounds.

FIG. 12 summarizes a technique wherein the maturation of the device pocket is assessed based on impedance using a pair of electrodes coupled to the device can. Many of the steps of this technique have already described above and hence will not be discussed again in detail. Briefly, at step 500, a pacemaker, ICD or CRT that has at least two device housing electrodes is implanted. FIG. 13 illustrates a pair of device housing "can" electrodes 502 and 504 of a device housing 506 that can be exploited to assess the maturation of the device pocket based on impedance. At step 508 of FIG. 12, the device applies impedance detection pulses or low-level high frequency AC signals using the pair of electrodes and measures voltage signals in response thereto to calculate impedance. At step 510, the device determines impedance response as a function of frequency for the device housing electrodes based either on the magnitude or phase of the impedance signal. At step 512, the device determines the degree of maturation of tissues encapsulating the device housing by: applying the impedance response values to look-up tables or templates representative of the particular type of tissue surrounding the device and its thickness to determine if the device is surrounded by mature tissues; and/or by assessing the degree of stability of the impedance signals over time. At step 514, the device records diagnostic information representative of the degree of maturation of the tissues encapsulating the device housing. In particular, the device can issue warning signals if the device pocket is not maturing as expected, as might be due to an infection in the device pocket. Then, at step 516, based on whether the degree of pocket maturation has reached an acceptable level, the device activates any impedance-based HF/PE detection vectors that utilize the device housing electrodes to detect possible HF/PE within the patient and/or control other device functions.

Figure 15:
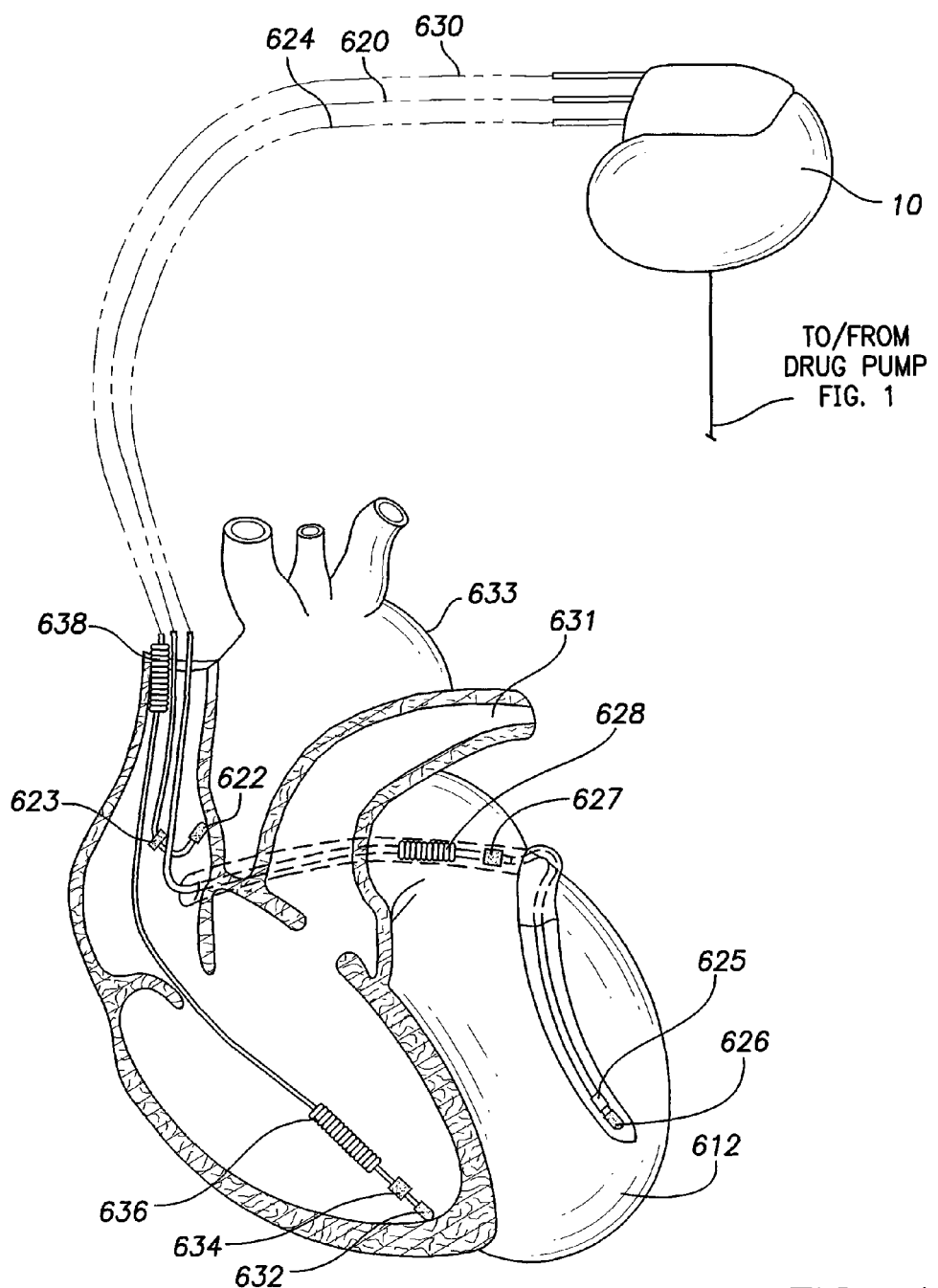
FIG. 15 is a simplified, partly cutaway view, illustrating the pacer/ICD/CRT of FIG. 1 along with a more complete set of exemplary leads implanted in the heart of a patient.

FIG. 13 summarizes an alternative technique wherein the maturation of the device pocket is assessed based on physiological sensor signals rather than impedance signals or AC current signals. Some of the steps of this technique have already described above and hence will not be discussed again in detail. Briefly, at step 550, a pacemaker, ICD or CRT having an internal 3D accelerometer, acoustic sensor or other "physiological sensor" capable of measuring sounds/vibrations affected by pocket maturation is implanted. FIG. 15, discussed below, illustrates exemplary physiological sensors. At step 552 of FIG. 12, the device measures sounds and/or vibrations using the physiological sensor, such as heart sounds or respiration sounds and the frequency band of those sounds. It is believed that before pocket maturation, blood and fluid in the pocket as well as the "looseness" of the device case will tend to damp out higher frequencies of sound. After maturation, the case is encapsulated in a stiffer substrate that allows higher frequency sounds to be transmitted. Hence, the frequency bandwidth of the detected sounds or vibrations can be used to assess device pocket maturity.

At step 554, the device then determines the degree of maturation of tissues encapsulating the device housing based on the sounds/vibrations by, e.g., applying values representative of the magnitude and/or frequency of the sounds/vibrations to look-up tables or templates representative of the particular type of tissue surrounding the housing—such as blood, thrombus, inflammatory tissue, myocardium, fibrosis, and endothelium—and its thickness to determine if the device pocket has matured. This may be performed using the same general techniques discussed above in connection with impedance frequency-response analysis but applied to the acoustic signals and their frequency bandwidths. Alternatively, the stability of the physiological signals is assessed over time. At step 556, the device records diagnostic information representative of the degree of maturation of the tissues encapsulating the device housing and warns if the device pocket is not maturing as expected. Then, at step 558, based on whether the degree of pocket maturation has reached an acceptable level, the device activates any impedance-based HF/PE detection vectors that utilize the device housing electrodes to detect possible HF/PE within the patient and/or to control other device functions. As noted above, the similarity or difference in impedance signal between the can and each of two or more distant and/or large electrodes (for example, can-to-RV coil and can-to-SVC coil) may be employed to ascertain the maturity of encapsulation in the device pocket. That is, the device can utilize two or more vectors including the case and at least one other electrode, as well as a vector including the "other" electrodes in those two or more vectors, to determine the near-field impedance at the case/device pocket. Following that determination, the assessment of maturity is completed.

Thus various techniques have been described that exploit electrical signals (impedance, AC current) or physiological signals (heart sounds, respiration sounds, vibrations, etc.) to assess encapsulation maturity. In some examples, these parameters are measured and compared only while the patient is at rest, for consistency. A sleep or circadian detector may be used to identify appropriate periods of time to measure the impedance values. In addition, posture detectors may be used to determine when the patient is in a certain predetermined posture (such as supine) so as to reduce or eliminate any variations in the measurement of the electrical or physiological parameters that may be due to changes in posture. See, e.g., posture detection techniques described in U.S. Pat. No. 6,658,292 of Kroll et al., entitled "Detection of Patient's Position and Activity Status Using 3D Accelerometer-Based Position Sensor." See, also, U.S. Pat. No. 7,149,579, cited above.

For the sake of completeness, a detailed description of an exemplary pacer/ICD/CRT device for performing or controlling the various techniques described above will now be provided. However, principles of invention may be implemented within other pacer/ICD/CRT implementations or within other implantable devices. Furthermore, although examples described herein involve processing of the various signals by the implanted device itself, some operations may be performed using an external device, such as a device programmer, computer server or other external system. For example, recorded data may be transmitted to an external device, which processes the data to evaluate encapsulation maturity based on impedance signals and/or to detect HF/PE during the acute phase based on non-impedance signals. Processing by the implanted device itself is preferred as that allows prompt detection of HF/PE and prompt activation of impedance-based HF/PE detection systems.

Exemplary Pacer/ICD

Figure 16:
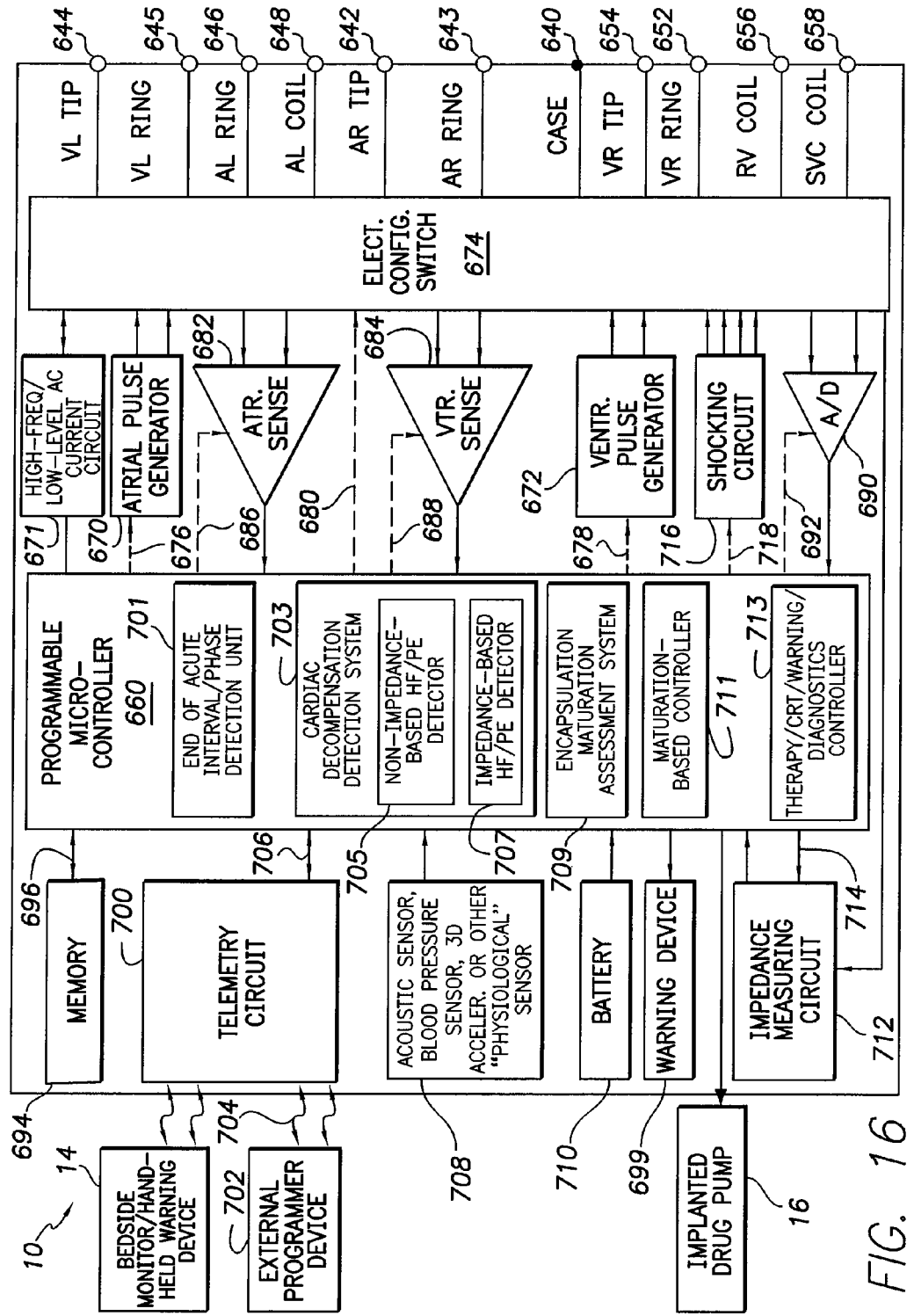
FIG. 16 is a functional block diagram of the pacer/ICD/CRT of FIG. 15, illustrating basic device circuit elements that provide cardioversion, defibrillation and/or pacing stimulation in four chambers of the heart and particularly illustrating components within the device for performing or controlling the techniques of FIGS. 2-14.

With reference to FIGS. 15 and 16, a description of an exemplary pacer/ICD will now be provided. FIG. 15 provides a simplified block diagram of the pacer/ICD, which is a dual-chamber stimulation device capable of treating both fast and slow arrhythmias with stimulation therapy, including cardioversion, defibrillation, and pacing stimulation, and also capable of performing or controlling the steps and functions discussed above. To provide other atrial chamber pacing stimulation and sensing, pacer/ICD 10 is shown in electrical communication with a heart 612 by way of a left atrial lead 620 having an atrial tip electrode 622 and an atrial ring electrode 623 implanted in the atrial appendage. Pacer/ICD 10 is also in electrical communication with the heart by way of a right ventricular lead 630 having, in this embodiment, a ventricular tip electrode 632, a right ventricular ring electrode 634, a right ventricular (RV) coil electrode 636, and a superior vena cava (SVC) coil electrode 638. Typically, the right ventricular lead 630 is transvenously inserted into the heart so as to place the RV coil electrode 636 in the right ventricular apex, and the SVC coil electrode 638 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a CS lead 624 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 624 is designed to receive atrial and ventricular cardiac signals and to deliver left ventricular pacing therapy using at least a left ventricular tip electrode 626 and a LV ring electrode 625, left atrial pacing therapy using at least a left atrial ring electrode 627, and shocking therapy using at least a left atrial coil electrode 628. With this configuration, biventricular pacing can be performed. Although only three leads are shown in FIG. 15, it should also be understood that additional leads (with one or more pacing, sensing and/or shocking electrodes) might be used and/or additional electrodes might be provided on the leads already shown.

A simplified block diagram of internal components of pacer/ICD 10 is shown in FIG. 16. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 640 for pacer/ICD 10, shown schematically in FIG. 16, is often referred to as the "can", "case" or "case electrode" and may be programmably selected to act as the return electrode for all "unipolar" modes. The housing 640 may further be used as a return electrode alone or in combination with one or more of the coil electrodes, 628, 636 and 638, for shocking purposes. In the alternative embodiment of FIG. 13, rather than using the device housing as a single can electrode, a pair of "can" or "case" electrodes are provided. In such an embodiment, additional case/case electrode terminals are provided, which are not shown in FIG. 16.

The housing 640 further includes a connector (not shown) having a plurality of terminals, 642, 643, 644, 645, 646, 648, 652, 654, 656 and 658 (shown schematically and, for convenience, the names of the electrodes to which they are connected are shown next to the terminals). As such, to achieve right atrial sensing and pacing, the connector includes at least a right atrial tip terminal ($A_R$ TIP) 642 adapted for connection to the atrial tip electrode 622 and a right atrial ring ($A_R$ RING) electrode 643 adapted for connection to right atrial ring electrode 623. To achieve left chamber sensing, pacing and shocking, the connector includes at least a left ventricular tip terminal ($V_L$ TIP) 644, a left ventricular ring terminal ($V_L$ RING) 645, a left atrial ring terminal ($A_L$ RING) 646, and a left atrial shocking terminal ($A_L$ COIL) 648, which are adapted for connection to the left ventricular ring electrode 626, the left atrial ring electrode 627, and the left atrial coil electrode 628, respectively. To support right chamber sensing, pacing and shocking, the connector further includes a right ventricular tip terminal ($V_R$ TIP) 652, a right ventricular ring terminal ($V_R$ RING) 654, a right ventricular shocking terminal ($V_R$ COIL) 656, and an SVC shocking terminal (SVC COIL) 658, which are adapted for connection to the right ventricular tip electrode 632, right ventricular ring electrode 634, the $V_R$ coil electrode 636, and the SVC coil electrode 638, respectively.

At the core of pacer/ICD 10 is a programmable microcontroller 660, which controls the various modes of stimulation therapy. As is well known in the art, the microcontroller 660 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 660 includes the ability to process or monitor input signals (data) as controlled by a program code stored in a designated block of memory. The details of the design and operation of the microcontroller 660 are not critical to the invention. Rather, any suitable microcontroller 660 may be used that carries out the functions described herein. The use of microprocessor-based control circuits for performing timing and data analysis functions are well known in the art.

As shown in FIG. 16, an atrial pulse generator 670 and a ventricular pulse generator 672 generate pacing stimulation pulses for delivery by the right atrial lead 620, the right ventricular lead 630, and/or the CS lead 624 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators or shared pulse generators. The pulse generators, 670 and 672, are controlled by the microcontroller 660 via appropriate control signals, 676 and 678, respectively, to trigger or inhibit the stimulation pulses. Additionally, a high frequency, low level AC current circuit 671 is provided for generating the aforementioned AC currents used to assess encapsulation maturity.

The microcontroller 660 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 674 includes a plurality of switches for connecting the desired electrodes to the appropriate I/O circuits, thereby providing complete electrode programmability. Accordingly, the switch 674, in response to a control signal 680 from the microcontroller 660, determines the polarity of the stimulation pulses (e.g., unipolar, bipolar, combipolar, etc.) by selectively closing the appropriate combination of switches (not shown) as is known in the art.

Atrial sensing circuits 682 and ventricular sensing circuits 684 may also be selectively coupled to the right atrial lead 620, CS lead 624, and the right ventricular lead 630, through the switch 674 for detecting the presence of cardiac activity in each of the four chambers of the heart. Accordingly, the atrial (ATR. SENSE) and ventricular (VTR. SENSE) sensing circuits, 682 and 684, may include dedicated sense amplifiers, multiplexed amplifiers or shared amplifiers. The switch 674 determines the "sensing polarity" of the cardiac signal by selectively closing the appropriate switches, as is also known in the art. In this way, the clinician may program the sensing polarity independent of the stimulation polarity. Each sensing circuit, 682 and 684, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 682 and 684, are connected to the microcontroller 660 which, in turn, are able to trigger or inhibit the atrial and ventricular pulse generators, 670 and 672, respectively, in a demand fashion in response to the absence or presence of cardiac activity in the appropriate chambers of the heart.

For arrhythmia detection, pacer/ICD 10 utilizes the atrial and ventricular sensing circuits, 682 and 684, to sense cardiac signals to determine whether a rhythm is physiologic or pathologic. As used in this section, "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 660 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 690. The data acquisition system 690 is configured to acquire intracardiac electrogram signals, convert the raw analog data into a digital signal, and store the digital signals for later processing and/or telemetric transmission to an external device 702. The data acquisition system 690 is coupled to the right atrial lead 620, the CS lead 624, and the right ventricular lead 630 through the switch 674 to sample cardiac signals across any pair of desired electrodes. The microcontroller 660 is further coupled to a memory 694 by a suitable data/address bus 696, wherein the programmable operating parameters used by the microcontroller 660 are stored and modified, as required, in order to customize the operation of pacer/ICD 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 694 through a telemetry circuit 700 in telemetric communication with the external device 702, such as a programmer, transtelephonic transceiver or a diagnostic system analyzer. The telemetry circuit 700 is activated by the microcontroller by a control signal 706. The telemetry circuit 700 advantageously allows intracardiac electrograms and status information relating to the operation of pacer/ICD 10 (as contained in the microcontroller 660 or memory 694) to be sent to the external device 702 through an established communication link 704.

Pacer/ICD 10 further includes an accelerometer or other physiologic sensor 708, sometimes referred to as a "rate-responsive" sensor because it can be used to adjust pacing stimulation rate according to the exercise state of the patient. Accordingly, the microcontroller 660 can respond by adjusting the various pacing parameters (such as rate, AV delay, VV delay, etc.) at which the atrial and ventricular pulse generators, 670 and 672, generate stimulation pulses. However, the physiological sensor 708 may further be used to detect patient posture, patient activity, blood pressure, and diurnal changes in activity (e.g., detecting sleep and wake states.) Additionally, as shown, the sensor can include 3D accelerometers or acoustic sensors for detecting heart sounds or respiratory sounds as well as changes in posture. While shown as being included within pacer/ICD 10, it is to be understood that all or part of the physiologic sensor 708 may be external to pacer/ICD 10, yet still be implanted within or carried by the patient. A common type of physiological sensor is an activity sensor incorporating an accelerometer or a piezoelectric crystal, which is mounted within the housing 640 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 710, which provides operating power to all of the circuits shown in FIG. 16. The battery 710 may vary depending on the capabilities of pacer/ICD 10. If the system only provides low voltage therapy, a lithium iodine or lithium copper fluoride cell typically may be utilized. For pacer/ICD 10, which employs shocking therapy, the battery 710 should be capable of operating at low current drains for long periods, and then be capable of providing high-current pulses (for capacitor charging) when the patient requires a shock pulse. The battery 710 should also have a predictable discharge characteristic so that elective replacement time can be detected. Accordingly, appropriate batteries are employed.

As further shown in FIG. 16, pacer/ICD 10 is shown as having an impedance measuring circuit 712, which is enabled by the microcontroller 660 via a control signal 714. Circuit 712 is used to detect impedance based either impedance pulses or on the AC currents for the various purposes described above. Additional uses for the impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 712 is advantageously coupled to the switch 774 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 660 further controls a shocking circuit 716 by way of a control signal 718. The shocking circuit 716 generates shocking pulses of low (up to 0.5 joules), moderate (0.5-10 joules) or high energy (11 to 40 joules or more), as controlled by the microcontroller 660. Such shocking pulses are applied to the heart of the patient through at least two shocking electrodes, and as shown in this embodiment, selected from the left atrial coil electrode 628, the RV coil electrode 636, and/or the SVC coil electrode 638. The housing 640 may act as an active electrode in combination with the RV electrode 636, or as part of a split electrical vector using the SVC coil electrode 638 or the left atrial coil electrode 628 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 7-40 joules or more), delivered asynchronously (since R-waves may be too disorganized), and pertaining exclusively to the treatment of fibrillation. Accordingly, the microcontroller 660 is capable of controlling the synchronous or asynchronous delivery of the shocking pulses.

An internal warning device 699 may be provided for generating perceptible warning signals to the patient via vibration, voltage or other methods.

Insofar as the acute phase processing techniques described above, the microcontroller includes an end of acute interval detection unit 701 operative to detect the end of the acute phase based, for example, on impedance stability or based on a programmed durations (such as forty-five days or sixty days.) The microcontroller also includes a cardiac decompensation detection system 703 operative to detecting cardiac decompensation events such as, HF, PE and CHF using the above-described techniques. In this example, system 703 includes a non-impedance-based HF/PE detector 705 operative to detect HF or PE or the like using non-impedance-based parameters, such as HRV, ventricular ER, etc. Detector 705 is provided especially for use during the post-implant acute phase, though it can operate during the chronic phase as well. System 703 includes an impedance-based HF/PE detector 707 operative to detect HF or PE or the like using impedance-based parameters (such as CI and PE impedances), once at least one pair of electrodes have been properly encapsulated by mature tissues.

Additionally, the microcontroller includes a component encapsulation maturation assessment system 709 operative to assess the degree of maturity of encapsulation of the components of the device, such as cardiac pacing/sensing electrodes using the techniques described above. A maturation-based controller 711 is operative to control various device functions based on the degree of maturation, such as to activate the impedance-based chronic interval HF/PE detector or to assess the progression of HF based on changes in the characteristic impedance response (amplitude and phase) of the tissue to bipolar AC impedance, as discussed above. Additionally, the microcontroller includes a therapy/CRT/warning/diagnostics controller 713 for controlling the delivery of therapy including CRT, the generation of warning signals and the recordation of diagnostics.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

As noted, at least some of the techniques described herein can be performed by (or under the control of) an external device. For the sake of completeness, an exemplary device programmer will now be described, which includes components for controlling at least some of the functions and steps already described.

Exemplary Device Programmer

Figure 17:
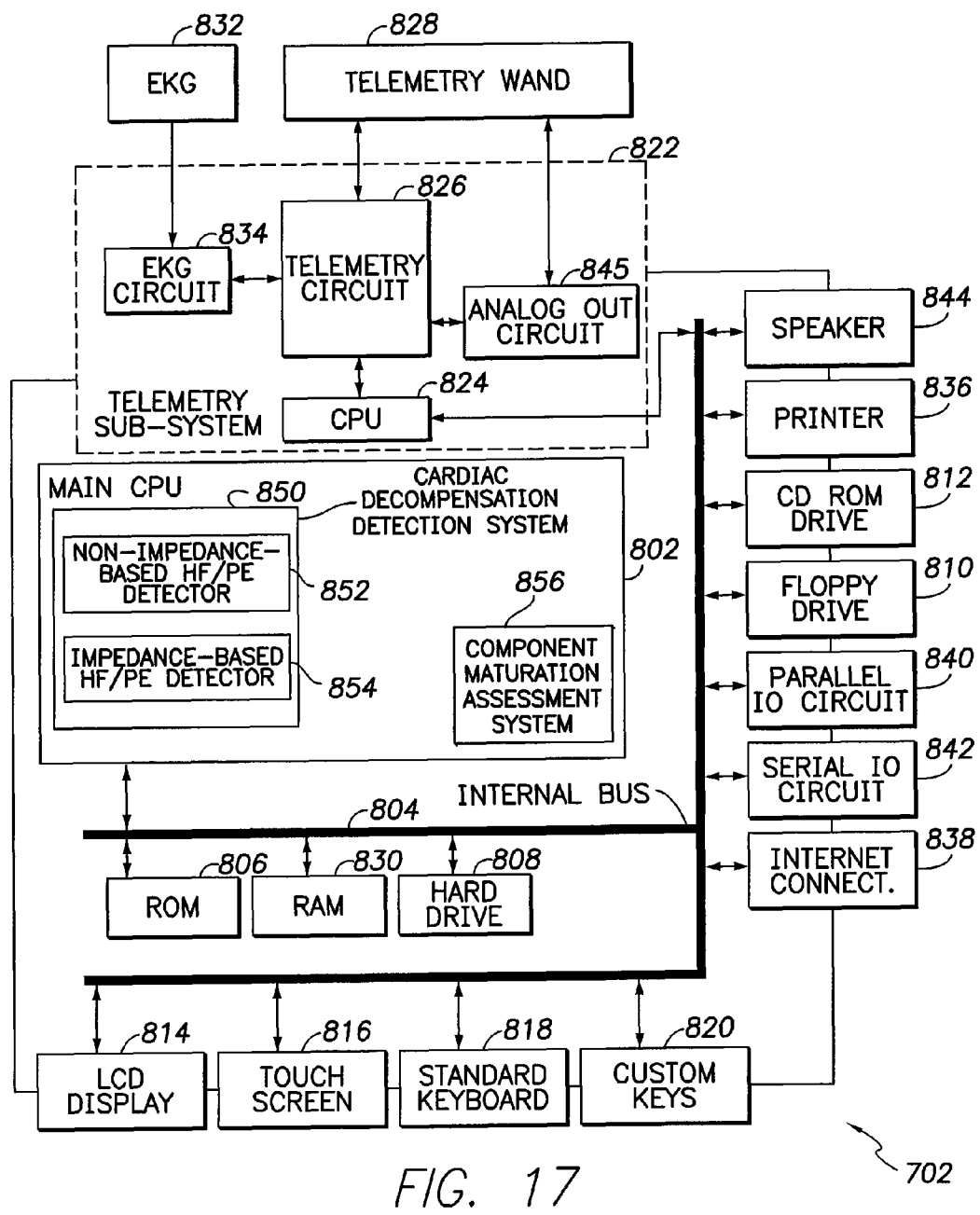
FIG. 17 is a functional block diagram illustrating components of a device programmer and in particular illustrating programmer-based components for performing or controlling the techniques of FIGS. 2-14 based on data sent from the implanted device.

FIG. 17 illustrates pertinent components of an external programmer 702 for use in programming the pacer/ICD of FIG. 16 and for performing the above-described optimization techniques. For the sake of completeness, other device programming functions are also described herein. Generally, the programmer permits a physician or other user to program the operation of the implanted device and to retrieve and display information received from the implanted device such as IEGM data and device diagnostic data. Additionally, the external programmer can be optionally equipped to receive and display electrocardiogram (EKG) data from separate external EKG leads that may be attached to the patient. Depending upon the specific programming of the external programmer, programmer 702 may also be capable of processing and analyzing data received from the implanted device and from the EKG leads to, for example, render preliminary diagnosis as to medical conditions of the patient or to the operations of the implanted device.

Now, considering the components of programmer 702, operations of the programmer are controlled by a CPU 802, which may be a generally programmable microprocessor or microcontroller or may be a dedicated processing device such as an application specific integrated circuit (ASIC) or the like. Software instructions to be performed by the CPU are accessed via an internal bus 804 from a read only memory (ROM) 806 and random access memory 830. Additional software may be accessed from a hard drive 808, floppy drive 810, and CD ROM drive 812, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 814 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 816 overlaid on the LCD display or through a standard keyboard 818 supplemented by additional custom keys 820, such as an emergency WI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various parameters are programmed. Typically, the physician initially controls the programmer 702 to retrieve data stored within any implanted devices and to also retrieve EKG data from EKG leads, if any, coupled to the patient. To this end, CPU 802 transmits appropriate signals to a telemetry subsystem 822, which provides components for directly interfacing with the implanted devices, and the EKG leads. Telemetry subsystem 822 includes its own separate CPU 824 for coordinating the operations of the telemetry subsystem. Main CPU 802 of programmer communicates with telemetry subsystem CPU 824 via internal bus 804. Telemetry subsystem additionally includes a telemetry circuit 826 connected to telemetry wand 828, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an EKG circuit 834 for receiving surface EKG signals from a surface EKG system 832. In other implementations, the EKG circuit is not regarded as a portion of the telemetry subsystem but is regarded as a separate component.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the pacer/ICD also includes the data stored within the recalibration database of the pacer/ICD (assuming the pacer/

ICD is equipped to store that data.) Data retrieved from the implanted devices is stored by external programmer 702 either within a random access memory (RAM) 830, hard drive 808 or within a floppy diskette placed within floppy drive 810. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 702, the implanted devices may be further controlled to transmit additional data in real time as it is detected by the implanted devices, such as additional IEGM data, lead impedance data, and the like. Additionally, or in the alternative, telemetry subsystem 822 receives EKG signals from EKG leads 832 via an EKG processing circuit 834. As with data retrieved from the implanted device itself, signals received from the EKG leads are stored within one or more of the storage devices of the external programmer. Typically, EKG leads output analog electrical signals representative of the EKG. Accordingly, EKG circuit 834 includes analog to digital conversion circuitry for converting the signals to digital data appropriate for further processing within the programmer. Depending upon the implementation, the EKG circuit may be configured to convert the analog signals into event record data for ease of processing along with the event record data retrieved from the implanted device. Typically, signals received from the EKG leads are received and processed in real time.

Thus, the programmer receives data both from the implanted devices and from optional external EKG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 802, the programming commands are converted to specific programmable parameters for transmission to the implanted devices via telemetry wand 828 to thereby reprogram the implanted devices. Prior to reprogramming specific parameters, the physician may control the external programmer to display any or all of the data retrieved from the implanted devices or from the EKG leads, including displays of EKGs, IEGMs, and statistical patient information. Any or all of the information displayed by programmer may also be printed using a printer 836.

Additionally, CPU 802 also preferably includes a cardiac decompensation detection system 850 operative to detect HF, PE, CHF or other cardiac decompensation events based on data signals sent from the implanted device. The detection system includes a non-impedance-based HF/PE detector operative to detect HF/PE or the like based on non-impedance signals such as HRV, ventricular ER, etc., as discussed above. The detection system includes an impedance-based HF/PE detector operative to detect HF/PE or the like based on impedance signals, as also discussed above. A component maturation assessment system 856 is operative to assess the maturity of encapsulation of device components, also as described above. Control parameters may then be transmitted to the pacer/ICD to program the device to perform deliver therapy to address any decompensation events that have been detected.

Programmer/monitor 702 also includes an Internet connection unit 838 such as a modem to permit direct transmission of data to other programmers via the public switched telephone network (PSTN) or other interconnection line, such as a T1 line or fiber optic cable, or wireless telecommunication system. Depending upon the implementation, the modem may be connected directly to internal bus 804 may be connected to the internal bus via either a parallel port 840 or a serial port 842. Other peripheral devices may be connected to the external programmer via parallel port 840 or a serial port 842 as well. Although one of each is shown, a plurality of input output (IO) ports might be provided. A speaker 844 is included for providing audible tones to the user, such as a warning beep in the event improper input is provided by the physician. Telemetry subsystem 822 additionally includes an analog output circuit 845 for controlling the transmission of analog output signals, such as IEGM signals output to an EKG machine or chart recorder.

With the programmer configured as shown, a physician or other user operating the external programmer is capable of retrieving, processing and displaying a wide range of information received from the implanted devices and to reprogram the implanted device if needed. The descriptions provided herein with respect to FIG. 17 are intended merely to provide an overview of the operation of programmer and are not intended to describe in detail every feature of the hardware and software of the programmer and is not intended to provide an exhaustive list of the functions performed by the programmer. Depending upon the implementation, the various components of the main CPU may be implemented as separate software modules or the modules may be combined to permit a single module to perform multiple functions. In addition, although shown as being components of the CPU, some or all of these components may be implemented separately from the microcontroller, using ASICs or the like.

In general, while the invention has been described with reference to particular embodiments, modifications can be made thereto without departing from the spirit and scope of the invention. Note also that the term "including" as used herein is intended to be inclusive, i.e. "including but not limited to."

What is claimed is:

1. A method for use with an implantable medical device for implant within a patient, the method comprising:
   during an acute interval following device implant;
   detecting a possible cardiac decompensation event within the patient using at least one detection parameter that is relatively insensitive to component encapsulation effects; and
   following the acute interval, detecting possible cardiac decompensation using at least one detection parameter that is relatively more sensitive to component encapsulation effects.

2. The method of claim 1 wherein the cardiac decompensation event includes one or more of heart failure (HF), congestive heart failure (CHF) and cardiogenic pulmonary edema (PE).

3. The method of claim 1 wherein detecting a possible cardiac decompensation event during the acute interval includes:
   sensing non-impedance-based cardiac decompensation detection parameters during the acute interval that are relatively insensitive to component encapsulation effects as compared to impedance-based detection parameters; and
   detecting the possible cardiac decompensation event during the acute interval using the non-impedance-based detection parameters.

4. The method of claim 3 wherein the non-impedance-based detection parameters include one or more of heart rate variability (HRV) parameters, ventricular evoked response (ER) parameters, atrioventricular (AV) delay parameters and interventricular (VV) delay parameters.

5. The method of claim 4 wherein the non-impedance-based detection parameters are supplemented using one or more of patient posture signals, patient activity signals and blood pressure signals.

6. The method of claim 4 wherein the ventricular ER parameters include one or more of a peak-to-peak ventricular ER amplitude parameter, a paced depolarization integral (PDI) parameter, and an ER T-wave minimum parameter.

7. The method of claim 4 wherein the AV delay parameters include one or more of a sensed AV delay, a paced AV delay, and the temporal variability of sensed and/or paced AV delay.

8. The method of claim 4 wherein the VV delay parameters include one or more of an LV-paced RV sense delay and an RV-paced LV sense delay.

9. The method of claim 1 wherein detecting a possible cardiac decompensation event following the acute interval includes:
    sensing impedance-based cardiac decompensation detection parameters following the acute interval that are relatively more sensitive to component encapsulation effects as compared to non-impedance-based detection parameters; and
    detecting the possible cardiac decompensation event following the acute interval using the impedance-based detection parameters.

10. The method of claim 9 wherein the impedance-based detection parameters include one or more of transthoracic impedance and intracardiac impedance using electrodes implanted within patient tissue.

11. The method of claim 9 further including:
    detecting the end of the acute interval; and
    switching from the non-impedance-based detection parameters to the impedance-based detection parameters upon detection of the end of the acute interval.

12. The method of claim 11 wherein the acute interval is deemed to end a predetermined number of days after implant.

13. The method of claim 11 wherein switching to the impedance-based detection parameters upon detection of the end of the acute interval is performed gradually.

14. The method of claim 11 wherein switching to the impedance-based detection parameters is performed substantially immediately.

15. The method of claim 11 wherein detecting the end of the acute interval includes:
    detecting impedance-based detection parameters to detect when impedance signals satisfy a predetermined stability criteria indicative of the end of the acute interval.

16. The method of claim 11 wherein detecting the end of the acute interval includes:
    detecting and examining non-impedance parameters to confirm an indication of signal stability.

17. The method of claim 9 wherein, following the acute interval, cardiac decompensation is detected using a combination of both impedance-based detection parameters and non-impedance-based detection parameters.

18. The method of claim 1 wherein, following the acute interval, cardiac decompensation is detected by applying a moving average window to detection parameters and wherein the duration of the moving average window increases with time until reaching a preferred duration.

19. A system for use with an implantable medical device for implant within a patient, the system comprising:
    an acute interval cardiac decompensation detection system operative during an acute interval following device implant to detect a possible cardiac decompensation event within the patient using one or more detection parameters that are relatively insensitive to component encapsulation effects; and
    a chronic interval cardiac decompensation detection system operative following the acute interval to detect a possible cardiac decompensation event within the patient using one or more detection parameters that are relatively more sensitive to component encapsulation effects.

20. A system for use with an implantable medical device for implant within a patient, the system comprising:
    means, operative during an acute interval following device implant, for detecting a possible cardiac decompensation event within the patient using one or more detection parameters that are relatively insensitive to component encapsulation effects; and
    means, operative following the acute interval, for detecting a possible cardiac decompensation event within the patient using one or more detection parameters that are relatively more sensitive to component encapsulation effects.

* * * * *